(12) United States Patent
Ebstein

(10) Patent No.: US 8,184,284 B2
(45) Date of Patent: May 22, 2012

(54) LASER-PROCESSED SUBSTRATE FOR MOLECULAR DIAGNOSTICS

(76) Inventor: Steven M. Ebstein, Newton, MA (US)

( * ) Notice: Subject to any disclaimer, the term of this patent is extended or adjusted under 35 U.S.C. 154(b) by 0 days.

(21) Appl. No.: 12/430,599

(22) Filed: Apr. 27, 2009

(65) Prior Publication Data

US 2009/0279085 A1  Nov. 12, 2009

Related U.S. Application Data

(63) Continuation-in-part of application No. 11/452,729, filed on Jun. 14, 2006, now Pat. No. 7,586,601.

(60) Provisional application No. 60/690,385, filed on Jun. 14, 2005, provisional application No. 61/125,453, filed on Apr. 25, 2008.

(51) Int. Cl.
*G01J 3/44* (2006.01)

(52) U.S. Cl. .......................................... 356/301

(58) Field of Classification Search .................. 356/300, 356/301, 72–73

See application file for complete search history.

(56) References Cited

U.S. PATENT DOCUMENTS

| | | | |
|---|---|---|---|
| 4,965,430 A | 10/1990 | Curtis et al. | |
| 5,057,184 A | 10/1991 | Gupta et al. | |
| 5,483,038 A | 1/1996 | Ota et al. | |
| 5,534,068 A | 7/1996 | Beach et al. | |
| 5,538,674 A | 7/1996 | Nisper et al. | |
| 5,557,409 A | 9/1996 | Downer et al. | |
| 5,580,655 A | 12/1996 | El-shall et al. | |
| 5,693,152 A | 12/1997 | Carron | |
| 5,770,022 A | 6/1998 | Chang et al. | |
| 5,994,164 A | 11/1999 | Fonash et al. | |
| 6,268,041 B1 | 7/2001 | Goldstein | |
| 6,294,442 B1 | 9/2001 | Kamal | |
| 6,300,193 B1 | 10/2001 | Forbes | |
| 6,376,177 B1 | 4/2002 | Poponin | |
| 6,406,777 B1 | 6/2002 | Boss et al. | |
| 6,917,726 B2 * | 7/2005 | Levene et al. | 385/12 |
| 7,057,256 B2 | 6/2006 | Carey, III et al. | |
| 7,354,792 B2 | 4/2008 | Carey, III et al. | |
| 7,442,629 B2 | 10/2008 | Mazur et al. | |
| 7,586,601 B2 | 9/2009 | Ebstein | |
| 2002/0149769 A1 | 10/2002 | Roorda et al. | |

(Continued)

FOREIGN PATENT DOCUMENTS

DE  20 2004 008 333  8/2004

(Continued)

OTHER PUBLICATIONS

Pedraza et al. (Laser-induced surface perturbations in silicon, Materials Research Society, vol. 16, No. 12, Dec. 2001).*

(Continued)

*Primary Examiner* — Tarifur Chowdhury
*Assistant Examiner* — Abdullahi Nur
(74) *Attorney, Agent, or Firm* — Pandiscio & Pandiscio

(57) ABSTRACT

Apparatus for use in performing a diagnostic assay of an analyte, the apparatus comprising a base that has been structured using laser processing so as to provide at least one patterned surface by melting and resolidification of the base, wherein the patterned surface is characterized by structures ranging in scale from 10 to 2000 nanometers and further wherein the pattern is stochastic in all three spatial dimensions; and a metal applied to the at least one patterned surface so as to provide at least one metalized patterned surface.

34 Claims, 13 Drawing Sheets

Example Raman Spectrum using SERS

U.S. PATENT DOCUMENTS

| | | |
|---|---|---|
| 2003/0029495 A1 | 2/2003 | Mazur et al. |
| 2003/0059820 A1 | 3/2003 | Vo-Dinh |
| 2003/0127441 A1 | 7/2003 | Haight et al. |
| 2003/0187237 A1 | 10/2003 | Chan et al. |
| 2003/0213715 A1 | 11/2003 | Klepac et al. |
| 2004/0101469 A1 | 5/2004 | Demers |
| 2004/0150818 A1 | 8/2004 | Armstrong et al. |
| 2004/0162554 A1 | 8/2004 | Lee et al. |
| 2004/0163758 A1 | 8/2004 | Kagan et al. |
| 2004/0259146 A1 | 12/2004 | Friend et al. |
| 2005/0084980 A1 | 4/2005 | Koo et al. |
| 2005/0112544 A1 | 5/2005 | Xu et al. |
| 2006/0038990 A1 | 2/2006 | Habib et al. |
| 2006/0079062 A1 | 4/2006 | Mazur et al. |
| 2006/0158653 A1 | 7/2006 | Chiarello et al. |
| 2006/0209413 A1 | 9/2006 | Kim et al. |
| 2006/0246573 A1 | 11/2006 | Kurane et al. |
| 2009/0014842 A1 | 1/2009 | Mazur et al. |
| 2009/0033929 A1 | 2/2009 | Mazur et al. |
| 2009/0046283 A1 | 2/2009 | Mazur et al. |
| 2010/0171948 A1 | 7/2010 | Mazur et al. |

FOREIGN PATENT DOCUMENTS

| | | |
|---|---|---|
| EP | 1 382 459 | 1/2004 |
| EP | 1 416 325 | 5/2004 |
| EP | 1 731 962 | 12/2006 |
| WO | WO 02/077608 | 10/2002 |
| WO | WO-2006/060734 | 6/2006 |
| WO | WO 2006/086014 | 8/2006 |
| WO | WO-2007/060989 | 5/2007 |
| WO | WO 2008/091852 | 7/2008 |
| WO | WO 2008/091858 | 7/2008 |

OTHER PUBLICATIONS

Vo-Dinh, Surface-Enhanced Raman Spectrometry With Silver Particles On Stochastic-Post Substrates, Analytical Chimica Acta, 1986 139-148, vol. 181.

Vo-Dinh et al., Plasmonics-Based Nanostructures for Surface-Enhanced Raman Scattering Bioanalysis, Methods in Molecular Biology, 2005, 255-283, vol. 300.

Henley et al., Excimer laser nanostructuring of nickel thin films for the catalytic growth of carbon nanotubes, Applied Physics Letters, 2004, 4035, 84.

Henley et al., Laser-Nanostructured Ag Films as Substrates for Surface-Enhanced Raman Spectroscopy, Applied Physics Letters, 2006, 081904, 88.

Lehmann, H.W. et al., Fabrication of submicron crossed square wave gratings by dry etching and thermoplastic replication techniques, Journal of Vacuum Science Technology, Oct.-Dec. 1983, pp. 1207-1210, vol. 1, No. 4.

Shuming Nie et al., Probing Single Molecules and Single Nanoparticles by Surface-Enhanced Raman Scattering, Science, Feb. 21, 1997, pp. 1102-1106, vol. 275.

Alan Campion et al., Surface-enhanced Raman scattering. Chemical Society Reviews, 1998, pp. 241-250, vol. 27.

Katrin Kneipp et al., Ultrasensitive Chemical Analysis by Raman Spectroscopy, Chemical Review, 1999, pp. 2957-2975, vol. 99.

Steven R. Emory et al., Direct Observation of Size-Dependent Optical Enhancement in Single Metal Nanoparticles, Journal of American Chemical Society, 1998, pp. 8009-8010, vol. 120.

Jorg P. Kottmann et al., Plasmon resonant coupling in metallic nanowires, Optics Express, Jun. 4, 2001, pp. 655-663, vol. 8, issue 12.

Jiang Jiang et al., Single Molecule Raman Spetroscopy at the Junctions of Large Ag Nanocrystals, Journal of Physical Chemistry, 2003, pp. 9964-9972, vol. 107.

Dentcho A. Genov et al., Resonant Field Enhancements from Metal Nanoparticle Arrays, Nano Letters, 2004, pp. 153-158, vol. 4, issue 1.

Yunwei Charles Cao et al., Nanoparticles with Raman Spetroscopic Fingerprints for DNA and RNA Detection, Science, Aug. 30, 2002, pp. 1536-1540, vol. 297.

Gang Logan Liu et al., Nanopillar substrate for SERS, Proceedings of the 7th International Conference on Miniaturized Chemical and Biochemical Analysis Systems, Oct. 5-9, 2003, pp. 705-708.

Gang Logan Liu et al., Configurable 3D Nanoscale High Aspect Ratio Pillars for Surface-Enhanced Raman Spectroscopy, IEEE, 2003, pp. 425-427.

Gang L. Liu et al., Nanowell surface enhanced Raman scattering arrays fabricated by soft-lithography for label-free biomolecular detections in integrated microfluidics, Applied Physics Letters, 2005, pp. 074101-1-074101-8, vol. 87.

R.P. Van Duyne et al., Atomic force microscopy and surface-enhanced Raman spectroscopy, I. Ag island films and Ag film over polymer nanosphere surffaces supported on glass, Journal of Chemical Physics, Aug. 1, 1993, pp. 2101-2115, vol. 99, issue 3.

Lucia G. Quagliano, The SERS Effect as a Tool for Studying Molecules Absorbed on Semiconductor Surfaces, The Internet Journal of Vibrational Spectroscopy, 2004, vol. 4, Edition 2.

Vladimir P. Drachev et al., Adaptive silver films towards bio-array applications.

Christy L. Haynes et al., Nanosphere Lithography: A Versatile Nanofabrication Tool for Studies of Size-Dependent Nanoparticle Optics, Journal of Physical Chemistry, 2001, pp. 5599-5611, vol. 105, issue 24.

Xiaoyu Zhang et al., An electrochemical surface-enhanced Raman spectoscopy approach to anthrax detection, Proceedings of SPIE, vol. 5221, pp. 82-91.

Vladimir P. Drachev et al., Adaptive Silver Films for Detection of Antibody-Antigen Binding, 2005, pp. 8368-8373, vol. 21, issue 18, Olga Lyandres et al., Real-Time Glucose Sensing by Surface-Enhanced Raman Spectroscopy in Bovine Plasma Facilitated by a Mixed Decanethiol/Mercaptohexanol Partition Layer, Analytical Chemistry, Oct. 1, 2005, pp. 6134-6139, vol. 77, issue 19.

C. Fagnano et al., Raman Spectroscopic Study of the Avidin-Biotin Complex, Journal of Raman Spectroscopy, 1995, pp. 991-995, vol. 26.

Richard P. Van Duyne et al., Spatially Resolved Surface Enhanced Raman Spectroscopy: Feasibility, Intensity Dependence on Sampling Area and Attomole Mass Sensitivity, May 2, 1986, pp. 190-196, vol. 126, issue 2.

Vladimir P. Drachev et al., Surface-Enhanced Raman Difference between Human Insulin and Insulin Lispro Detected with Adaptive Nanostructures, Journal of Physical Chemistry, 2004, pp. 18046-18052, vol. 108.

Katrin Kneipp et al., Single Molecule Detection Using Surface-Enhanced Raman Scattering (SERS), Physical Review Letters, Mar. 3, 1997, pp. 1667-1670, vol. 78, issue 9.

Christy L. Haynes et al., Plasmon Scanned Surface-Enhanced Raman Scattering Excitation Profiles, Materials Research Society Symposia Proceedings, 2002, pp. 7.1-7.6, vol. 728.

T.-H. Her et al., Femtosecond laser-induced formation of spikes on silicon, Applied Physics A Materials Science & Processing, 2000, pp. 383-385, vol. 70.

M.Y. Shen et al., Femtosecond laser-induced formation of submicrometer spikes on silicon in water, Applied Physics Letters, Dec. 6, 2004, pp. 5694-5696, vol. 85, issue 23.

M.Y. Shen et al., Formation of regular arrays of silicon microspikes by femtosecond laser irradiation through a mask, Applied Physics Letters, pp. 1715-1717, vol. 82, issue 11.

Paul E. Laibinis et al., Comparison of the Structures and Wetting Properties of Self-Assembled Monolayers of n-Alkanethiols on the Coinage Metal Surfaces, Cu, Ag, Au. Journal of The American Chemical Society, 1991, pp. 7152-7167, vol. 113.

Ganesh D. Sockalingum et al., Raman and SERS spectroscopy for probing drug-target interactions: from in-vitro models to intracellular imaging, Internet Journal of Vibrational Spectroscopy.

S. Astilean et al., Ordered Metallic Nanostructures For Surface-Enhanced Raman Spectroscopy, Romanian Reports in Physics, 2004, pp. 346-351, vol. 56, issue 3.

J.G. Bergman et al., Relationship between surface-enhanced Raman scattering and the dielectric properties of aggregared silver films, Optics Letters, Jan. 1981, pp. 33-35, vol. 6, issue 1.

Kenji Katayama et al., Formation of ring patterns surrounded by ripples by single-shot laser irradiation with ultrashort pulse width at the solid/liquid interface, Applied Physics Letters, Jun. 16, 2003, pp. 4244-4246, vol. 82, No. 24.

James M. Sylvia et al., Surface-Enhanced Raman Detection of 2,4-Dinitrotoluene Impurity Vapor as a Marker To Locate Landmines, Analytical Chemistry, Dec. 1, 2000, pp. 5834-5840, vol. 72.

Devesh C. Deshpande et al., Investigation of femtosecond laser assisted nano and microscale modifications in lithium niobate, Journal of Applied Physics, Mar. 29, 2005, p. 74316, vol. 97.

Naoki Yasumaru et al., Nanoscale modification of DLC film surfaces with femtosecond laser pulses, Proceedings of the SPIE—The International Society for Optical Engineering, 2004, pp. 755-759, vol. 5662.

N.V. Tarasenko et al., Laser-induced modification of metal nanoparticles formed by laser ablation technique in liquids, Applied Surface Science, Feb. 19, 2005, pp. 418-422, vol. 247, Nos. 1-4.

Michael S. Pio et al., Batch Fabrication nanopillars for autonomous nanofluidic SERS arrays, Materials Research Society Symposium Proceedings, Apr. 1, 2002, pp. 179-184, vol. 729.

Katrin Kneipp et al., Surface-enhanced Raman scattering and biophysics, Journal of Physics: Condensed Matter, May 13, 2002, pp. R597-R624, vol. 14, No. 18.

G. Daminel et al., Femtosecond laser interaction with silicon under water confinement, Thin Solid Films, 2004, pp. 334-341, vol. 467.

Ajit P. Jogelkar et al., Optics at critical intensity: Applications to nanomorphing, Proceedings of the National Academy of Sciences of the United States of America, Apr. 20, 2004, pp. 5856-5861, vol. 101, No. 16.

D.J. Hwang et al., Liquid-assisted femtosecond laser drilling of straight and three-dimensional microchannels in glass, Applied Physics A, 2004.

N. Yasumaru et al., Femtosecond-laser-induced nanostructure formed on hard thin films of TiN and DLC, Applied Physics A, 2003, pp. 983-985, vol. 76.

T.H.R. Crawford et al., Sub-wavelength surface structures on silicon irradiated by femtosecond laser pulses, 2003.

A.J. Pedraza et al., Laser induced surface perturbations in silicon, Journal of Materials Research, Dec. 2001, pp. 3599-3608, vol. 16, No. 12.

V. Studer et al., Nanoembossing of thermoplastic polymers for microfluidic applications, Applied Physics Letters, May 13, 2002, pp. 3614-3616, vol. 80, No. 19.

Anthony J. Pedraza et al., Generation and manipulation of nanostructures by pulsed-laser processing, Proceedings of SPIE, 2002, pp. 164-174, vol. 4760.

D.G. Georgiev et al., Controllable excimer-laser febrication of conical nano-tips on silicon thin films, Applied Physics Letters, Jun. 14, 2004, 4881-4883, vol. 84, No. 24.

S. Chan et al., Surface-Enhanced Raman Scattering of Small Molecules from Silver-Coated Silicon Nanopores, Advanced Materiels, Oct. 2003, 1595-1598, vol. 15, issue 19.

Surojit Chattopadhay et al., Surface-Enhanced Ramon Speotroscopy Using Self-Assembled Silver Nanoparticles on Silicon Nanotips, Chemistry of Materials, 2005, 553-559, vol. 17, issue 3.

Chih-Hsun Hsu et al., Generally Applicable Self-Masked Dry Etching Technique for Nanotip Array Fabrication, Nano Letters, 2004, 471-475, vol. 4, issue 3.

* cited by examiner

Example Raman Spectrum using SERS

SERS spectra of fBAP on the ASF substrate (blue) and the same fBAP-modified surface after incubation with fAb solution (red); (A) nine spectra, each obtained from three spots; (B) average of the nine spectra.
Label-free antibody-antigen binding Time-varying (kinetics) SERS signal for glucose partitioning by a self-assembled monolayer Raman spectra of A) avidin, B) avidin-biotin, C) trytophan, D) biotin in the lyophilized form Nanostructured silicon surface formed by femtosecond laser irradiation at two different magnifications.

Stainless steel surface nanostructured with femtosecond laser pulses and micropatterned with a hexagonal mask. Note that the structure near the mask boundary is partially ordered while in the interior, the surface is stochastic.

Nanostructured metal surfaces formed by femtosecond laser irradiation. The left image shows a titanium surface and copper is shown at the right. Scale bar is 1 μm at left, 5 μm at right.

Nanowires are formed on silicon when the femtosecond laser processing is done with an organic solvent in place of water, like in Fig. 5. This figure shows a surface processed with methanol. The left image has a 20 μm scale bar. The right image has a 2 μm scale bar, and is positioned at the edge of the region that was laser processed.

Scanning electron micrographs of ordered silicon spikes formed by masking the irradiated sample with (a), (b) a 30 μm hexagonal grid and (c), (d) a 20 μm square grid. The nearly Gaussian spatial intensity profile of the laser pulse is shown at the top in grayscale (white corresponds to maximum intensity).

Scanning electron micrographs of (a)–(e) silicon spikes formed with a square grid after increasing number of laser pulses. The direction of the electric field is vertical in (a)–(e). (f) Spikes formed with the grid rotated 45° relative to the grids in (a)–(e).

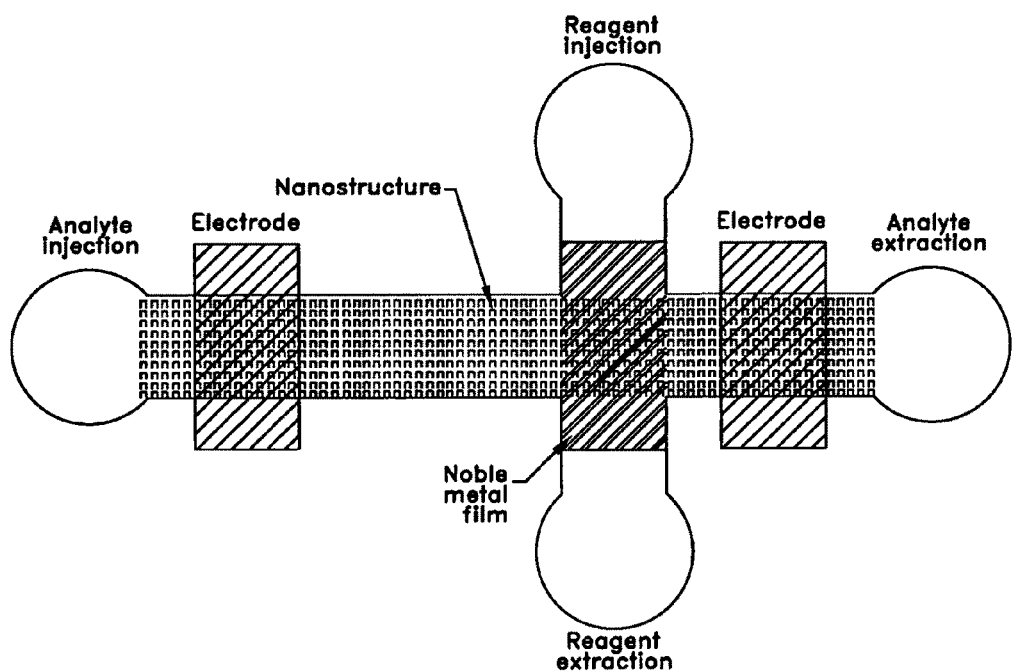

Example device incorporating microfluidic delivery of a reagent, and separation via electro-osmotic pressure. Analyte is injected through a port at the left. A voltage is placed across the two electrodes to effect separation as ions migrate through the nanostructure. A reagent is injected at the appropriate time through the top port. A noble metal film enables surface enhanced detection, e.g., SERS, of a reaction product.

FIG. 12

Silicon nanostructured with femtosecond laser pulses. The pulse energy increases from (a) to (b), as does the spatial scale of the structure. The scale bar in the inset in (a) is 1 μm.

LASER-PROCESSED SUBSTRATE FOR MOLECULAR DIAGNOSTICS

REFERENCE TO PENDING PRIOR PATENT APPLICATIONS

This patent application:

(i) is a continuation-in-part of prior U.S. patent application Ser. No. 11/452,729, filed Jun. 14, 2006 now U.S. Pat. No. 7,586,601 by Steven M. Ebstein for APPLICATIONS OF LASER-PROCESSED SUBSTRATE FOR MOLECULAR DIAGNOSTICS, which patent application in turn claims benefit of pending prior U.S. Provisional Patent Application Ser. No. 60/690,385, filed Jun. 14, 2005 by Steven M. Ebstein for APPLICATIONS OF LASER-PROCESSED SUBSTRATE FOR MOLECULAR DIAGNOSTICS; and (ii) claims benefit of pending prior U.S. Provisional Patent Application Ser. No. 61/125,453, filed Apr. 25, 2008 by Steven M. Ebstein for APPLICATIONS OF LASER-PROCESSED SUBSTRATE FOR MOLECULAR DIAGNOSTICS.

The three above-identified patent applications are hereby incorporated herein by reference.

FIELD OF THE INVENTION

The present invention pertains to an apparatus and a method for quantitatively detecting and distinguishing between compounds, especially biomolecules, with high sensitivity and selectivity using a laser-processed substrate and an optical source and detector.

BACKGROUND OF THE INVENTION

Molecular diagnostics are an increasingly important part of biotechnology. The ability to detect small quantities of genomic, proteomic, and other biological materials enables sensitive clinical tests to be performed, as well as enabling laboratory research that affects drug development and functional biology. Molecular sensing modalities include radioactivity, mass spectroscopy, and electrical and optical techniques. The worldwide market for molecular biomarkers, diagnostics, and related services exceeded $6 billion in 2003.

While current technology is quite useful, it is not as sensitive or as specific as is desired, and there is room for improvement in the speed and economics of the diagnostics. The utility of many current genomic assays is limited by the need to replicate sample material using techniques like Polymerase Chain Reaction (PCR), which can add inaccuracies, take time to process, and may add cost through royalty payments. Even with large material samples, the results of gene chip readers have significant statistical variation. Consequently, there is great interest in techniques that improve the ability to unambiguously detect specific molecules in very small quantities. Nanotechnology has been identified as one approach that can potentially improve the sensitivity of molecular diagnostics.

My new approach, which will hereinafter be discussed, is to use a novel family of nanostructured substrates to develop a sensitive optical technique for molecular diagnostics that uses Surface Enhanced Raman Scattering (SERS) or other optical detection techniques. Raman spectroscopy is a non-invasive technique that requires little material preparation and can provide an essentially unique signature for biological and many other molecules. Nanometer-scaled conducting structures, through coupling to surface plasmon modes, can greatly enhance the Raman signal so that the diagnostic can be performed in a practical setting with minute amounts of material.

I will hereinafter discuss the use of a novel nanostructured substrate that satisfies all of the requirements for successful application of SERS to molecular diagnostics. Namely, the novel nanostructured substrate is inexpensive to produce, it can be precisely tailored for maximally enhancing the Raman signal, and it can easily be micropatterned for use as an array. As I detail below, the novel substrate can also be used to separate analytes that are in solution with the use of microfluidics and electrochemistry that are easily co-manufactured. The novel substrate has a large effective surface area and can be tailored to enhance additional optical detection techniques such as fluorescence. This enables the substrate to serve as a platform for a variety of molecular diagnostics.

In vitro molecular diagnostics can be performed with a variety of sensing modalities that measure optical, electrical, radioactive, or mass spectroscopic properties of the material under test (i.e., the analyte). In most scenarios, the analyte is processed so it is selectively bonded to a compound in the apparatus. Sometimes either the analyte or a mating compound is tagged with a label such as a fluorophore, nanosphere, or another agent that is then detected to indicate the presence and/or concentration of the principal analyte or analytes.

The present invention is, among other things, concerned with a photonic diagnostic technique (e.g., Raman spectroscopy utilizing Surface Enhanced Raman Scattering, or SERS) that can be label-free and may or may not require the analyte to be bonded to another compound.

Raman scattering is the process whereby an optical photon inelastically scatters off a molecule by coupling with the vibrational modes of the molecule. The scattered photon energy is reduced (Stokes) or augmented (anti-Stokes) by the energy of the vibrational mode. The Raman scattered light has a detailed spectrum that is essentially unique for biological and many other molecules as it encodes all of the bonds present in the molecule, and may indicate the conformation of the molecule as well. Raman spectroscopy (RS) is the technique whereby the spectrum is measured by quantitatively recording the Raman scattered light as a function of wavelength or wavenumber ($cm^{-1}$) when a monochromatic (e.g., a laser) beam illuminates the sample. An example of a Raman spectrum is shown in FIG. 1.

One barrier to the use of Raman spectroscopy is the small cross-section for Raman scattering, a factor of $\sim 10^{14}$ less than the cross-section for fluorescence. This problem is mitigated when the molecule is adsorbed onto, or is near, a conductive surface with structure at the appropriate nanometer-sized scale. Then, the incident electromagnetic field, e.g., the laser, the plasmon modes of the conduction electrons, and the molecular vibrational modes strongly couple and greatly enhance the Raman scattering cross-section. This electromagnetic (EM) enhancement can increase the cross-section by up to a factor of $10^{14}$, locally, and by a factor of $10^4$-$10^8$ averaged over the ensemble of molecules nearby or adsorbed on a conducting surface. In addition to the EM enhancement, additional enhancement can come from chemical interactions or from a resonance of the molecule with the input laser (i.e., the Raman pump) wavelength. The latter effect is usually termed Surface Enhanced Resonance Raman Scattering (SERRS).

The basic correlation of nanoscale structure and surface plasmon excitation is apparent from Mie scattering theory. The characteristic structure size for effective SERS enhancement ranges from tens of nm for isolated metal particles to several hundred nm for nanostructured surfaces. The optimum feature size for maximum enhancement scales with the pump wavelength. Both theoretical and experimental studies have shown that the EM enhancement is maximized where particles are nearly or actually touching, or generally where the surface is discontinuous and electric fields are presumed to be large. There is evidence that periodic structures increase the SERS enhancement. However, it is generally acknowledged that detailed knowledge and prediction of the surface enhancement phenomenon is not completely understood at this time.

Many substrates have been used for SERS. Initial work used metal electrodes that were electrochemically etched to produce nanoscale roughness. Those substrates were particularly unpredictable and often changed their properties over time due to electrochemical reactions. Molecules in solution have been analyzed with SERS by introducing nano-sized metal particles into the solution. These particles have included silver and other metal colloids and, more recently, nano-sized spheres that are produced by a variety of means. Over the years, SERS substrates have generally been made by forming a nanostructure, then evaporating a metalized layer onto the nanostructure. The underlying substrate has included lithographically etched materials, chemically etched materials, and a self-assembled monolayer of plastic nanospheres. Additional techniques for forming SERS substrates involve evaporating metal films onto glass slides—this can include depositing metal islands on the glass slide by not uniformly covering the surface of the slide, and nanopatterning the surface of the slide by using the interstices of a self-assembled nanosphere layer as apertures in a technique called nanosphere lithography. Recently, a substrate has been announced that uses a metalized photonic crystal formed by semiconductor lithography. Another substrate with interesting properties, but which is probably not affordably manufacturable, is e-beam lithography of silicon.

The interest in SERS as an analytical technique comes from several features. The signal from SERS can be larger than the fluorescence signal due to the surface enhancement and the shorter lifetime of Raman excitation relative to fluorescence, which can enable more scattering events per molecule per unit time. The SERS spectrum is typically 10~100 times narrower than the typical fluorescence spectrum. This addresses one serious issue with fluorescence studies, i.e., the number of different labels that can be distinguished in the same assay. With fluorescence labels, a maximum of 12 labels can be distinguished. This number can increase, significantly, if SERS-active labels are used. At least one company, Nanoplex Technologies, Inc. of Mountain View, Calif., is focused on developing labeling nanoparticles that are SERS-active.

Moreover, the SERS spectrum is essentially unique for each analyte. This offers the opportunity to identify specific analytes that do not need to be labeled with a fluorescent dye. This same feature can also enable label-free binding detection. Many assays are designed to measure the binding or conjugation of two complementary materials—e.g., a protein-ligand, a DNA strand-oligonucleotide, etc. The SERS spectrum has been shown by to exhibit variation that indicates when binding has occurred, as is seen in FIG. 2. SERS has been used to quantitatively detect the amount of an analyte and measure time-varying signals indicative of binding kinetics, as is seen in FIG. 3. For the case of a protein (avidin) and a small molecule (biotin), a Raman spectral signature of the bound complex shows variation in the protein spectrum (tryptophan bands) and the presence of a biotin peak at 690 $cm^{-1}$ which has information about the structure and function of the bound complex, as is seen in FIG. 4.

With the surface enhancement in SERS analyses, very small quantities of material can be detected using spatially-resolved detection. Some experiments have achieved atto-mole sensitivity and, for isolated particles, detection of single molecules has been achieved. There have been numerous papers on SERS and related studies of plasmon resonance with nanoscaled structures. There have been hundreds of papers per year on this topic since 1995.

As many of the advantages of SERS have been known for years, and with the level of interest in the literature, it is instructive to understand why SERS analysis has not become more prevalent. One major reason often cited in the literature is the lack of availability of a suitable substrate material. Many substrates exhibit a wide variation in sensitivity from realization to realization, or over time. Other substrates are expensive or difficult to prepare. The development of quantitative analysis using SERS depends on the availability of substrates that are relatively easy and inexpensive to produce, are readily reproducible, and offer the potential to tailor the surface features for strong Raman scattering enhancement. While some of the SERS substrates I have described above meet one or more of these criteria, no substrate is currently commercially available that meets all of them.

SUMMARY OF THE INVENTION

In accordance with the present invention, a novel substrate is provided, a region of whose surface is pre-processed with a laser to yield a nanometer-scaled structure and which has a metal film applied to the nanostructured region so as to form the novel substrate. In some cases, the substrate can comprise an appropriate metal so that the laser-processing provides the nanometer-scaled metal structures desired for SERS applications—in these cases, the subsequent step of applying a metal film to the laser-processed surface may be omitted.

In one form of the invention, a means of introducing a cell or a solution or mixture (i.e., the analyte) to that nanostructured, metalized region is provided so that the analyte is either adsorbed onto the region, or lies in solution covering the region, or is deposited as a powder on the region, or is a gaseous vapor adjacent to the region, whereby to facilitate SERS analysis of the analyte.

And in one form of the invention, a means of separating or fractionating the solution or mixture (i.e., the analyte) is provided.

And in another form of the invention, a means of introducing a reagent to the solution or mixture (i.e., the analyte) is provided.

A detection apparatus is provided consisting of (i) a light source to irradiate the nanostructured, metalized region (or a portion thereof) and the analyte, and (ii) an optical detector to sense the scattered radiation. In particular, a narrowband laser and a spectrometer are provided which determine the Surface Enhanced Raman Spectrum (SERS) of the analyte material near the nanostructured, metalized surface.

In one preferred form of the invention, there is provided a method for sensing at least one of the presence and quantity of an analyte, wherein the method comprises:

providing a base that has been structured using laser processing so as to provide at least one patterned surface;

applying a metal to the at least one patterned surface so as to provide at least one metalized patterned surface; and using the at least one metalized patterned surface as a substrate for performing a diagnostic assay of the analyte.

In another form of the invention, there is provided an apparatus for use in performing a diagnostic assay of an analyte, the apparatus comprising:

a base that has been structured using laser processing so as to provide at least one patterned surface; and a metal applied to the at least one patterned surface so as to provide at least one metalized patterned surface.

In another form of the invention, there is provided a substrate for sensing at least one of the presence and quantity of an analyte introduced to the substrate, the substrate comprising:

a base that has been structured using laser processing so as to provide at least two patterned surfaces; and a metal applied to the at least two patterned surfaces so as to provide at least two metalized patterned surfaces.

In another form of the invention, there is provided a substrate for sensing at least one of the presence and quantity of an analyte introduced to the substrate, the substrate comprising:

a base that has been structured using laser processing so as to provide at least one patterned surface; and a metal applied to the at least one patterned surface so as to provide at least one metalized patterned surface;

wherein the base comprises at least one via for directing the analyte across the at least one metalized patterned surface.

In another form of the invention, there is provided an apparatus for sensing at least one of the presence and quantity of an analyte, the apparatus comprising:

a base that has been structured using laser processing so as to provide at least one patterned surface;

a metal applied to the at least one patterned surface so as to provide at least one metalized patterned surface; and an optical characterization module comprising:
a light source for directing light at an analyte disposed on the at least one metalized patterned surface; and
a detector that measures the light scattered by the analyte.

In another form of the invention, there is provided a method for sensing at least one of the presence and quantity of an analyte, wherein the method comprises:

providing a casting base that has been structured using laser processing so as to provide at least one casting base patterned surface;

duplicating the base by casting so as to provide a working base having at least one working patterned surface;

applying a metal to the at least one working patterned surface so as to provide at least one metalized patterned surface; and using the at least one metalized patterned surface as a substrate for performing a diagnostic assay of the analyte.

In another form of the invention, there is provided apparatus for use in performing a diagnostic assay of an analyte, the apparatus comprising:

a base that has been structured using laser processing so as to provide at least one patterned surface by melting and resolidification of the base, wherein the patterned surface is characterized by structures ranging in scale from 10 to 2000 nanometers and further wherein the pattern is stochastic in all three spatial dimensions; and a metal applied to the at least one patterned surface so as to provide at least one metalized patterned surface.

In another form of the invention, there is provided an assembly comprising:

a metal base that has been structured using laser processing so as to provide at least one patterned surface by melting and resolidification of the base, wherein the patterned surface is characterized by structures ranging in scale from 10 to 2000 nanometers and further wherein the pattern is stochastic in all three spatial dimensions; and an analyte disposed on the at least one patterned surface.

In another form of the invention, there is provided a method for sensing at least one of the presence and quantity of an analyte, wherein the method comprises:

providing a base that has been structured using laser processing so as to provide at least one patterned surface characterized by structures extending in all three spatial dimensions, wherein the laser processing comprises the selective application of pulsed laser energy to the base whereby to melt a surface layer of the base which resolidifies so as to create the structures of the at least one patterned surface, and further wherein the melting across the laser spot is non-uniform with fine structure on scales comparable to the resulting structures of the patterned surface;

applying a metal to the at least one patterned surface so as to provide at least one metalized patterned surface, wherein the at least one metalized patterned surface has a surface profile configured to provide large electric fields when electromagnetic energy is delivered to the at least one metalized patterned surface;

positioning the analyte on the at least one metalized patterned surface; and performing a diagnostic assay of the analyte by delivering electromagnetic energy to the analyte and/or the at least one metalized patterned surface.

In another form of the invention, there is provided a method for sensing at least one of the presence and quantity of an analyte, wherein the method comprises:

providing a base that has been structured using laser processing so as to provide at least one patterned surface characterized by structures extending in all three spatial dimensions, wherein the laser processing comprises the selective application of pulsed laser energy to the base whereby to melt a surface layer of the base which resolidifies so as to create the structures of the at least one patterned surface, and further wherein the melting across the laser spot is non-uniform with fine structure on scales comparable to the resulting structures of the patterned surface;

positioning the analyte on the at least one patterned surface; and performing a diagnostic assay of the analyte by delivering electromagnetic energy to the analyte and/or the at least one patterned surface.

BRIEF DESCRIPTION OF THE DRAWINGS

These and other objects, features and advantages of the present invention will be more fully disclosed or rendered obvious by the following detailed description of the preferred embodiments of the invention, which is to be considered together with the accompanying drawings wherein like numbers refer to like parts, and further wherein:

FIG. 12 is a schematic view of an exemplary device incorporating microfluidic delivery of a reagent, and separation via electro-osmotic pressure, wherein analyte is injected through a port at the left, the voltage is placed across the two electrodes to effect separation as ions migrate through the nanostructure, a reagent is injected at the appropriate time through the top port, and a noble metal film enables surface enhanced detection, e.g., SERS, of a reaction product;

Figure 1:
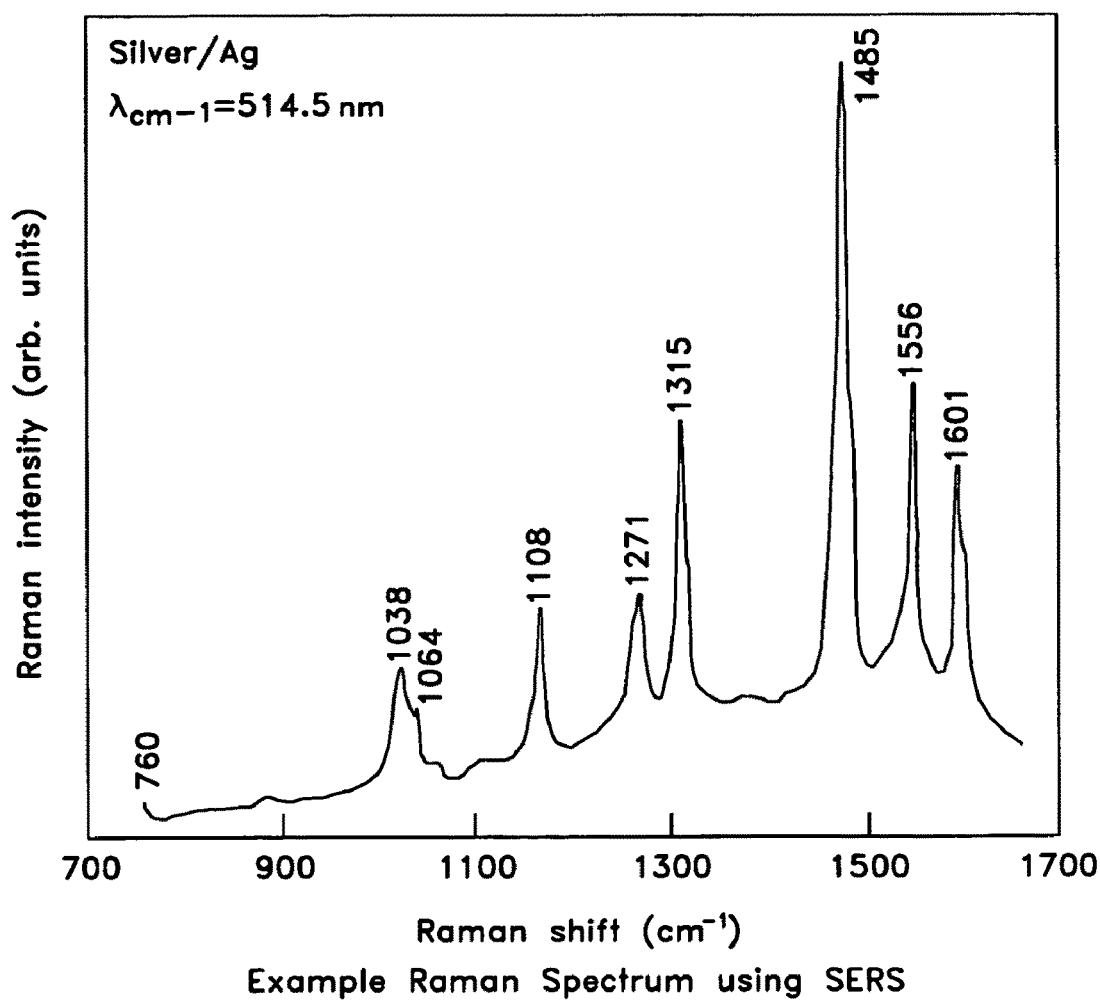
FIG. 1 is a schematic view of an exemplary Raman spectrum using SERS.
Figure 2:
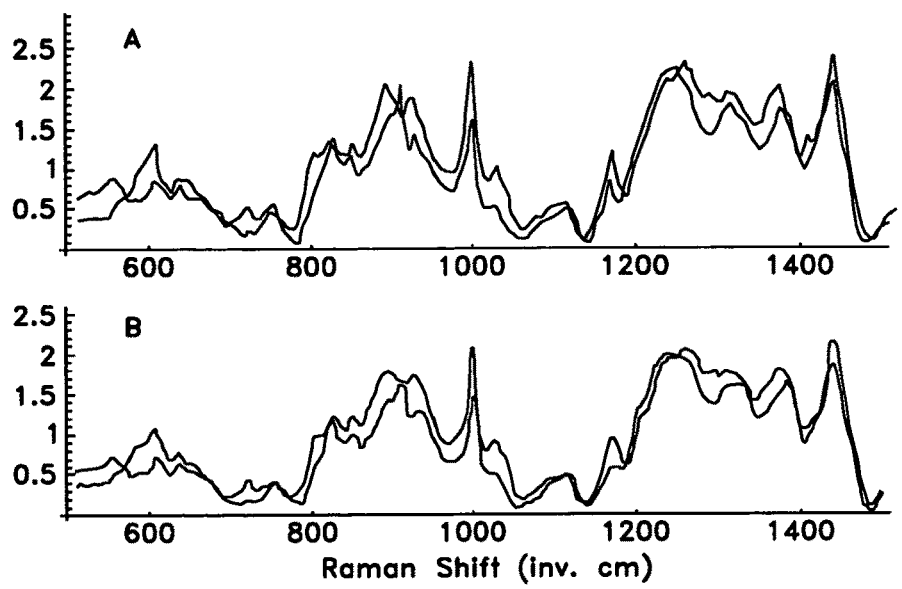
FIG. 2 is a schematic view of a SERS spectra associated with label-free antibody-antigen binding.
Figure 3:
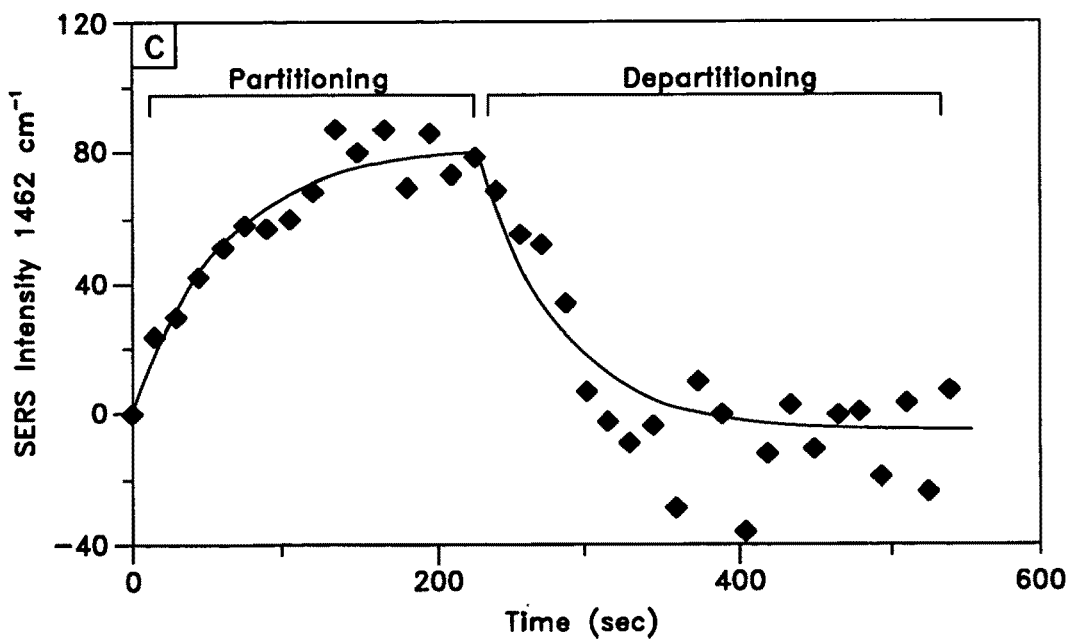
FIG. 3 is a schematic view of a time-varying (kinetic) SERS signal for glucose partitioning by a self-assembled monolayer.
Figure 4:
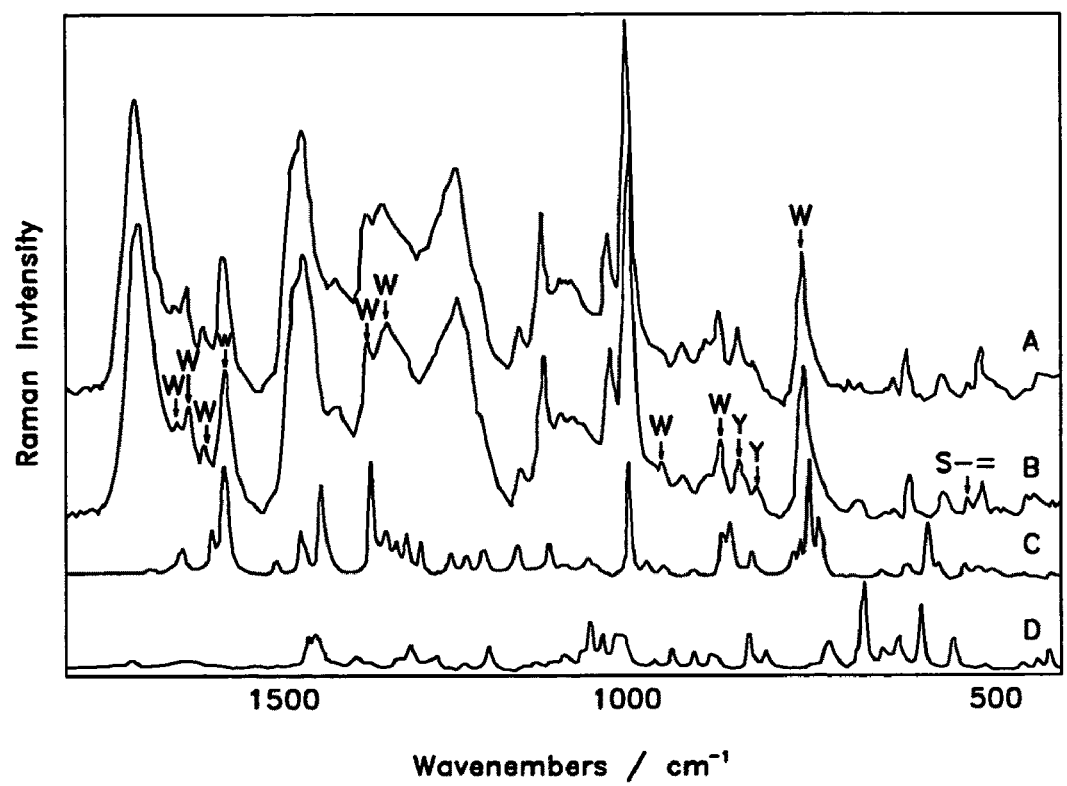
FIG. 4 is a schematic view showing the Raman spectra of A) avidin, B) avidin-biotin, C) tryptophan, and D) biotin in the lyophilized form.

It should be appreciated that the drawings are intended to provide a better understanding of the present invention, but they are in no way intended to limit the scope of the invention.

DETAILED DESCRIPTION OF THE PRESENT INVENTION

A novel substrate that meets all of the criteria discussed above for effecting surface enhancement of an analyte for SERS analyses is formed by a novel semiconductor or metal structure which includes nanopatterned surfaces fabricated by laser processing using femtosecond lasers. The femtosecond laser irradiation of the semiconductor or metal structure (e.g., silicon) in the appropriate environment can produce a variety of interesting nanostructures. These nanostructures are either produced in a metal substrate or the nanostructured surface is subsequently metalized so as to form the complete substrate which can provide the desired optical effect, e.g., for SERS applications.

One such structure is called black silicon, as micron-scale spikes formed on the surface of the silicon change the reflectivity of the silicon so its absorptance is significantly increased in the visible, and well into the infrared, spectrum.

Another structure has nanoscale bumps or spikes when the base material is covered with water, or another liquid, during laser processing.

Another member of this family of structures involves the irradiation of metal surfaces which can produce nanosized cylindrical asperities along the surface.

Yet another surface geometry which may be used in the present invention is the growth of thin nanowires which can result when an organic solvent covers the surface, e.g., methanol over silicon, during laser processing.

These nanopatterned structures are shown in FIGS. 5-9.

While the dynamics of forming the desired nanopatterned surface structures using femtosecond lasers is not thoroughly understood at this time, the basic explanation is that the energy deposition by the femtosecond pulse excites surface waves in the base material. Diffraction by the surface structure further roughens the structure that then 'freezes' in place as the laser heating is removed. Non-uniformities induced in the laser beam before it is incident on the surface can also play a role in the laser structuring process. The effect of multiple pulses can be seen in FIG. 6.

It will be appreciated that the laser structuring process involves melting and resolidification that rearranges the substrate material in the desired manner. More particularly, this process produces a surface structure with random features in all 3 dimensions, both along the plane of the substrate and perpendicular to the plane of the substrate. In other words, this laser structuring of the substrate provides a structured surface characterized by a stochastic pattern in all three spatial dimensions due to random aspects of the structuring process, with the laser-induced structures having the spatial characteristics desired for SERS applications.

Details for forming microstructured or nanostructured surfaces using femtosecond lasers are provided in:

(i) U.S. Provisional Patent Application Ser. No. 60/293, 590, filed May 25, 2001 for SYSTEM AND METHODS FOR LIGHT ABSORPTION AND FIELD EMISSION USING MICROSTRUCTURAL SILICON;

(ii) U.S. patent application Ser. No. 10/155,429, filed May 24, 2002 by James E. Carey, Catherine Crouch, Claudia Wu, Rebecca Younkin, and Eric Mazur for SYSTEM AND METHODS FOR LIGHT ABSORPTION AND FIELD EMISSION USING MICROSTRUCTURAL SILICON;

(iii) U.S. patent application Ser. No. 10/950,230, filed Sep. 24, 2004 by James E. Carey and Eric Mazur for SILICON-BASED VISIBLE AND NEAR-INFRARED OPTOELECTRIC DEVICES;

(iv) U.S. patent application Ser. No. 10/950,248, filed Sep. 24, 2004 by James E. Carey and Eric Mazur for MANUFACTURE OF SILICON-BASED DEVICES HAVING DISORDERED SULFUR-DOPED SURFACE LAYERS;

(v) U.S. patent application Ser. No. 11/196,929, filed Aug. 4, 2005 by Eric Mazur and Mengyan Shen for FEMTOSECOND LASER-INDUCED FORMATION OF SUBMICROMETER SPIKES ON A SEMICONDUCTOR SUBSTRATE; and (vi) International (PCT) Patent Application No. PCT/US05/34180, filed Sep. 23, 2005 by Eric Mazur and James E. Carey for MANUFACTURE OF SILICON-BASED DEVICES HAVING DISORDERED SULFUR-DOPED SURFACE LAYERS.

The foregoing six patent applications are hereby incorporated herein by reference.

The nanopatterned surface structures may then be metalized by the deposition of a noble metal film so as to form a novel substrate which can serve to effect the desired surface enhancement of an analyte for optical analyses. More particularly, nanopatterned surface structures, after application of a noble metal film, satisfy all the criteria for a SERS substrate. Alternatively, the laser processing may be performed on an appropriate metal substrate, in which case the subsequent metallization step may be omitted. The surface characteristics of the nanostructured material may be tailored by adjusting (i) the energy of the laser pulse, and (ii) the manner in which the pulse train is delivered to the substrate. This allows one to tailor the nanostructured substrate so that the final metalized surface has the right scales for SERS enhancement. The nanostructured surfaces are straightforward to fabricate with commercially-available femtosecond lasers. With a 20 W femtosecond laser, an area equivalent to an entire 25 mm×75 mm microscope slide can be fabricated in less than 2 minutes, so this material can be manufactured at a reasonable cost. Due to the fact that femtosecond pulses deposit energy before it can diffuse, the energy deposition, and hence the statistical properties of the nanopatterned surface, are predictable and reproducible if the laser pulses are delivered in a controlled fashion.

As surface plasmon modes are excited when any metal is irradiated with a laser, it will be appreciated that any nanostructured metal surface exhibits some enhancement of the induced electric field. Thus, in some cases, useful substrates can be fabricated by laser patterning of a metal base without a subsequent metalization step. The enhancement factor is likely to be greatest when a noble or coinage metal is structured, e.g., gold, silver, or copper.

When laser patterning is performed, the surface of the material being structured is subject to intense electric fields, which can ionize the surface material or the fluid which is in contact with the surface, whether it is a gas or liquid. This ionized material can be very reactive and cause the surface material to undergo a chemical reaction. Consequently, a structured metal surface may not have a pristine layer of the metal at the surface, which will generally reduce the enhancement of any induced electric fields. In some cases, it may have a thin, oxidized layer.

Thus, in some situations, a subsequent step may be desirable or required to treat the structured metal surface when metal substrates are directly laser-patterned without a subsequent metallization step. More particularly, in order to form a useful surface, well-known chemical or electrochemical processing may be employed to etch away or convert the modified surface layer into a pristine metal which will exhibit greater enhancement. This chemical or electrochemical processing will vary with the base material and the character of the surface structure induced with laser patterning.

Laser-nanostructured substrates have been demonstrated to provide a useful base for devices which incorporate subsequent metallization and can be used as substrates for molecular detection using surface enhanced Raman spectroscopy (SERS). Substrates nanostructured by processing with an ultrafast (femtosecond) laser have been fabricated in silicon, stainless steel, titanium and copper. This processing has used 400 nm wavelength lasers with the substrate material in a water bath. The laser wavelength and aspects of the surrounding medium such as its refractive index and thermal properties have some influence on the details of the nanostructure. The resulting metal nanostructure should be tailored to the particular Raman laser wavelength(s) which may be employed in the SERS application. It is generally desirable to produce columnar structures which have a controlled, high-aspect ratio (height to width/separation), since such columnar structures have been demonstrated (theoretically and experimentally) to produce large enhancement factors.

My previous disclosures have described irradiating an area of the substrate material with a laser spot. The workpiece and the laser spot are relatively translated (i.e., moved relative to one another) in order to cover a larger area. The effective time that the spot dwells on a particular spot affects the depth and details of the nanostructure that is produced. For instance, a slower relative feed rate means that each spot on the material "sees" more laser pulses. This has been shown to produce deeper nanostructures with more pulses. The absorption/reflectivity of the material is a function of the nanostructure depth, among other factors, so there is an optimal depth for a particular wavelength of Raman laser.

My previous disclosures have also described placing a mask over the substrate material. In general, these masks have holes with diameters measured in microns. This has the effect of forming arrays of structured material, and also affects the details of the nanostructure inside the structured regions. For example, the boundary conditions of the illumination at the edge of a mask aperture appear to induce some order in the nanostructure, at least in the direction perpendicular to the aperture boundary.

Among other things, the present disclosure introduces several new ideas that may improve the speed or efficiency with which the surface is structured. The goal is to produce nanopatterned surfaces with a given surface morphology, i.e., spatial pattern of bumps, pillars or spikes. In the following discussion, I will address the formation of nanopillars, but this is intended to be without loss of generality. As the laser melts a layer of material at the surface, which then flows and resolidifies, tailoring the portion of the surface that is melted could improve the speed or efficiency of that operation. For example, it is possible that by only melting the portions of the surface which are intended to end up as troughs of the final surface, the pillars will form more quickly and the rate of processing of the surface could increase.

One way to accomplish this is to structure the laser light which irradiates the substrate surface. For example, the laser light could be split into two or more beams which are then recombined at an angle to form a fringe pattern or other pattern that has alternating light and dark regions. The melting will preferentially occur at the light regions, which will presumably end up as the troughs of the surface, while the dark regions will melt less and will presumably end up as the pillars.

The laser beam can be split and recombined using well-known beam-splitters, mirrors, and lenses. However, since I generally want to produce nanostructured regions, the various beams will have to combine at relative large angles which makes the required optics difficult to construct. In addition, the motion of the workpiece relative to the structured light must leave the nanostructure surface aligned with the structured light. Since this can require the motion to be periodic with nanometer periods, it can be expensive to accomplish. So, other ways of modifying the spatial melting of the substrate may be preferred.

Another way to pattern the melting by the laser is to structure the incident laser beam by passing it through an optical mask that has a nanostructured pattern, e.g., a master mask with 100 nm diameter holes. For example, a chrome-on-glass mask can be nanopatterned with standard lithography techniques (either light-based or ion-based). The mask can then be placed between the structuring laser beam and the substrate material. The chrome material will generally reflect the laser, defining regions which are melted less, while the clear regions will pass the laser, defining regions which are melted more. If the mask is fixed relative to the substrate material, the melting pattern will remain fixed, avoiding the problem with structuring the light. Other masks, such as a thin metal mask, may be preferred. It will be appreciated that these thin metal masks have fine structure that is much smaller than the dimensions of the laser spot, thereby efficiently promoting the laser structuring of the substrate on that fine scale.

This approach also has some technical difficulties, since the distance between the mask and the substrate material cannot be too large or diffraction can spoil the intensity pattern defined by the mask. The small distance will affect the volume of liquid which is present to cool the substrate material, and may be evaporated by the structuring laser. It is possible to flow liquid in the gap between a mask and the substrate material, or use a mask thin enough so it can be placed on the substrate material. It is also possible to arrange the path which the structuring laser makes across the substrate material, and to arrange the flow path of the liquid, so the irradiated region is always covered with liquid.

Another way to impose a pattern on the material which is melted is by imprinting a pattern on the surface of the substrate material that affects the local absorption of the incident laser radiation. One way to do that is to deposit a material that enhances either the absorption or reflection of the laser light. For example, using standard photolithographic techniques, a thin layer of inorganic material can be deposited on the substrate material. The substrate material is coated with photoresist which is then illuminated with the pattern. Depending on whether negative or positive processing is used, the substrate can be processed so either the exposed or unexposed regions are left with the inorganic material, leaving a nanopattern. Nanoimprint lithography, using a nanostructured tool to print a patterned, thin layer of material like a printing press, is another cost-effective means of depositing material that could seed the nanostructure formation.

Another way to cause non-uniform melting across the laser spot in order to improve the efficiency of the laser processing is to deposit a layer of an inhomogeneous material on the surface which is to be structured. This deposited material ideally has inhomegeneities on nanometer scales and is ideally applied in a thin layer that may consist of a monolayer or less, on average, of the material. It may be sprayed, spin-coated or drip-coated onto the substrate. One example is the application of a self-assembling monolayer of plastic nanospheres, which will result in a non-uniform incident flux of the structuring laser onto the substrate.

It will be appreciated that the various methods of applying a non-uniform absorber or reflector to the substrate all require the applied pattern to have fine structure that is much smaller than the dimensions of the laser spot, thereby efficiently promoting the laser structuring of the substrate on that fine scale.

Another way to affect the local absorption is to do a preliminary structuring of the surface with the processing laser and a mask. Here, the mask is only used initially to modify the surface in a way that seeds the subsequent structuring, rather than keeping the mask in place during the entire structuring process. This may be more efficient in its use of the laser light, since the attenuating mask is only present initially, and it may prolong the lifetime of the mask.

The foregoing are some examples of ways to modify the absorption or reflection of the substrate material so that the structuring laser can produce the resulting nanostructure more efficiently. They also offer a way by which the morphology of the surface can be controlled, since they obviously affect the transverse spatial pattern of the nanostructure. It should be appreciated that the foregoing examples are offered by way of example but not limitation.

With simple masks and appropriate delivery of the femtosecond pulse train, the surface of the substrate can be micropatterned with a series of nanopatterned regions. If the boundary conditions of the processed surface are controlled, the resulting structure self-organizes into a quasi-periodic pattern. FIGS. 7-11 show examples of micropatterned regions that exhibit stochastic and quasi-periodic structures at different scales and in different regions of the surface.

The ability to micropattern the surface of the base material (e.g., a semiconductor or metal material) and do other laser machining is particularly interesting for the application of this novel substrate to arrays. Microarrayed patterns of nanostructures can be fabricated that will allow these substrates to be used in a manner similar to microarrays that are used for genomic and proteomic screening. For scenarios where specific detection of molecular species can be performed without labeling the molecules, as must be done for fluorescence detection, the resulting arrays can have greater specificity and sensitivity than conventional microarrays and eliminate the need to do PCR replication, which also adds noise.

Other desirable features relating to microfluidics and electrochemistry can easily be co-manufactured and add additional functionality to the novel substrate. For example, the same femtosecond laser used to nanostructure the surface can also be used to ablate material and machine micro- and nano-vias in the substrate. Adding a cover to the substrate forms channels that can be used to direct fluid flow across the substrate. This can be accomplished by placing a flat cover material on the substrate and allowing liquid surface tension to hold the cover in place. In addition, the cover material can be glued or thermally bonded to the base material. One possible material for the cover, commonly used in micro- and nano-fluidic devices, is polydimethylsiloxane (PDMS).

A unique advantage of this approach for forming a SERS substrate is the ability to make deep or high-aspect nanostructures that are precisely tailored. No other approach, except perhaps porous silicon produced by etching, can affordably make similarly convoluted structures, and those structures are poorly controlled. One benefit of my substrate is that the effective surface area of the substrate is much larger than the planar area of the substrate. This greatly increases the volume of analyte that can be placed in close proximity to the metal films deposited on the nanostructures and supporting the plasmon modes, and thus increases the dynamic range of the measurement.

When the nanostructured region is covered with a cap or other cover, the result is a nanoporous channel. This feature can be used to separate or fractionate different materials that are introduced via a solution or mixture to the substrate. The separation can occur as the result of differential flow resistance to fluid pressure or as the solutes or mixture components are subjected to electro-osmotic pressure by applying a voltage across a non-conducting substrate, or can occur due to electrophoresis of ionic species in solution.

A flow of analyte across the substrate can also be coupled with functionalization of the substrate to enable more complex detection. For example, an analyte mixture flowed over the substrate could possibly contain different compounds which have different chemical properties. Different regions on the substrate could be coated with different materials that preferentially attract or repel certain compounds. Examples of such coatings could be oligonucleotides, proteins, or antibodies to which specific molecules can bind. They can also be coatings which, for example, attract or repel molecules with specific chemical groups, ionic charges, or pH values. The regions on the substrate can be ordered along the direction of the flow, perpendicular to the flow, or in a matrix which is correlated with a complex flow pattern that may involve movement of solution or solute in multiple directions. Spatially variable functionalization of the substrate and material flow are coupled with time-varying optical, e.g., Raman spectral measurements, in order to detect particular analytes that match a spatial or temporal pattern that depends on the functionalization.

It should be appreciated that a metalization step may be necessary in order to introduce the thin noble metal film onto the laser-generated nanostructures. As a result, metalization for other purposes can be effected without significantly complicating the substrate fabrication procedure. Thus, for example, by placing a mask over the substrate before metalization, electrodes can be patterned on the substrate. This allows a voltage to be applied along a channel that is formed in the substrate which will cause various ions in the solution or mixture to migrate along the channel at rates that depend on the size of the ions and the porosity of the channel. These electrodes also enable other electrochemical reactions to be driven.

An example of a complex structure involving microfluidics and electrochemistry is shown in FIG. 12.

Other features of the substrate can control how an analyte, introduced to the substrate in liquid form, is moved or held in place. For instance, the surface of the substrate can be machined such that structures are formed that confine a small liquid drop which can be spotted onto the surface. In addition, the surface of the substrate can be coated with various materials that either promote or inhibit adhesion and adsorption onto the surface. A common technique to promote adhesion is to apply a self-assembled monolayer of molecules with a thiol group at the end. If the thiol group is added to the end of a molecule that binds with the analyte of interest, the analyte will be bound to the surface.

Surface composition and chemistry plays a number of roles in using these novel substrates. Surface composition and chemistry can protect the surface and affect the durability and shelf life of the substrates. And surface composition and chemistry affects whether the analyte adsorbs onto the substrate, thereby enabling the SERS effect. Surface composition and chemistry also affects how the various conjugate targets—genomic, proteomic, and other biomolecules—can be bound to the surface. Surface composition and chemistry can also affect how material introduced to the substrate is confined.

It is desirable that the substrate properties for surface enhancement be stable over time. It is also desirable that the substrate not be susceptible to being attacked by a solution that is introduced for analysis. While no material remains pristine forever, it is generally necessary to inhibit oxidation of the metal film, especially if silver is used. It is also desirable to minimize any reaction of the analyte or solution with the substrate, since that could change the behavior of molecules in solution and the coupling with the plasmon modes of the metal film. Since many analytes of interest are presented in a saline solution, the surface should resist corrosion by salt water.

One solution is to protect the surface of the substrate with a very thin overcoat that inhibits chemical reactions but is thin and transparent enough that it does not change the optical properties and the ability of molecules to get close to the metal film. There are at least three different approaches to overcoating the surface.

First, it is possible to add a thin overcoat of glass (e.g., silicon dioxide) to the substrate. Depositing a thin film of silicon using a vapor deposition process, followed by oxidation, can produce this layer. This approach has the advantage that the protective layer is glass, for which almost any subsequent functionalization that is required has already been developed.

A second approach is to cover the nanopatterned surface of the substrate with a self-assembled monolayer (SAM). Most often thiols, these SAMs are short (several nm in length) linear molecules for which the thiol group readily attaches to metals such as gold. There are numerous literature examples for SAM attachment to silver and other metals as well. This approach has the advantage that molecules can be used with functional groups that bind to target molecules which are used to functionalize the surface. There can be some concern that a SAM on a convoluted surface will not cover uniformly and will have defects. However, as long as the defects in the monolayer are a small fraction of the total area, this should not be a problem. Since the SAMs are deposited from a liquid, there is less concern that regions that are hard to reach will be covered. This is my preferred approach for overcoating nanopatterned surfaces of the substrate.

This approach has been used by other researchers to functionalize surfaces used for SERS substrates. For example, SAMS have been used to functionalize surfaces so that glucose could be partitioned from solution in order to attach enough material to give a significantly large SERS signal.

The SAMs must be chosen for stability, both with respect to degradation before the substrate is used and also with respect to use with analyte and washing solutions.

A third approach for overcoating the nanopatterned surfaces of the substrate is to apply a very thin parylene coating. Parylene is a substance deposited by gas-phase polymerization which process is able to uniformly cover surfaces with a pinhole-free coating. However, the desired thickness for the SAMs, tens of nm at most, is thinner than most parylene coatings and it may require new engineering to apply the parylene coating uniformly.

Another aspect of protecting the nanopatterned and metalized surface is to keep it pristine until used. Note that in addition to the coatings that may be applied, the substrates will generally be stored and shipped in inert atmospheres such as nitrogen or argon.

The ability of various analyte molecules to adsorb onto the nanopatterned surface and to coat the surface with target molecules depends on the compatibility and affinity of the two materials (i.e., the analyte material and the substrate material), and whether the substrate can be wetted. There is also an issue of non-specific adsorption by analytes in a mixture. Although the substrates should be functionalized with as specific an agent as possible, the SERS spectrum could provide sufficient information to look for the presence of the target analytes even if other analytes adsorb. This can become a matter of signal-to-noise, where finding a molecule that is a small fraction of a mixture is more difficult than one that is the dominant species.

Minimizing non-specific adsorption will improve the signal-to-noise ratio. It may be accomplished by a combination of functionalization and the use of blocking agents. For example, if a certain protein is the target molecule, the surface might be functionalized with a SAM to which the protein adheres. After the protein is bound to the surface, it may be useful to block any remaining surface with a neutral agent that does not affect the part of the SERS spectrum used to measure binding. Milk protein and Human Serum Albumin (HSA) have previously been used for this purpose with other SERS substrates.

I discuss in general terms how each of the protective coatings could be coated with materials with the desired properties. If the metal films are overcoated with glass, then there are numerous commercial agents and processes that can be used to functionalize them so biomolecules of interest will adsorb or adhere to them. For example, Gelest, Inc. of Morrisville, Pa. sells silane agents that are used to functionalize glass slides for DNA, proteins, or cells.

If the metal films (overcoating the nanopatterned structures of the substrate) themselves are overcoated with SAMs, the SAM molecule must be chosen so the free end (not attached to the metal) has the right functional group attached, i.e., an aldehyde, amine, or carboxyl group. Dojindo Molecular Technologies, Inc. of Gaithersburg, Md., is a commercial vendor of SAMs which can be deposited onto the metalized layer.

If a parylene coating is used, the polymer must first be oxidized before a functional group can be added. This can be done in a weak air plasma, after which the desired receptors can be added.

In general, the analyte is introduced to the substrate in liquid form. Consequently, how the analyte is confined to a region on the substrate is determined by how liquids interact with the surface of the substrate. The liquid should wet the region where measurements will be made. It may be helpful to have boundary regions that do not wet around these wetted areas so as to confine the liquid.

This is particularly important when using the substrates as microarrays. It is possible to use a combination of (i) micromachining and (ii) tailoring the surface wetting properties, to direct drops of spotted solution to remain in a particular region so a large array of experiments can be performed without cross-contamination. There are several approaches to confining the spotted material.

The first approach involves the generation of selective surface roughness to confine spotted drops. In general, flatter surfaces are wetted more easily than rough ones. It is possible to pattern an array with two different levels of surface roughness using the laser processing I have discussed above. The active part of the array would comprise isolated small regions with laser processed nanostructures appropriate for SERS. The inactive (or confining) part of the array would be the intervening grid pattern. This inactive region could be laser processed to produce microstructured black silicon so that it is much rougher than the neighboring nanostructured material. This structuring would ensure that a drop would preferentially wet the nanostructured region with its smaller roughness.

A second approach involves patterning the surface with different chemical treatments. One example of a process for producing a hydrophobic grid surrounding isolated regions is as follows. A silicon wafer is coated with Teflon or another hydrophobic agent. A metal mask with small (e.g., 50 micron square) holes can be placed over the wafer. The femtosecond laser is used to first ablate the hydrophobic agent from the small squares, and subsequently to form the SERS nanostructures. With the mask still in place, the nanostructured regions are metalized and any further surface treatment is done. Then the mask is removed, leaving the hydrophobic agent under the masked pattern.

The greatly increased surface area of the substrate is another feature of the invention that offers advantages over competing approaches. The nanostructured material has a much greater surface area than a similar sized flat surface. This enables greater amounts and concentrations of reagents or binding materials to be deposited when the surface is functionalized and increases the resulting reaction rates and/or fractions of material that participate in the reaction.

A variety of techniques can be used to introduce analyte to the substrate in solid, liquid, or gaseous form. Some examples are to spot a drop onto the substrate, either manually or robotically, and allow the solvent to evaporate. Alternatively, a cover slip could be placed over the drop spotted onto the substrate to analyze molecules in solution. If a cover with a fluid port is bonded onto the substrate, the liquid could be pumped onto the substrate in an example of a microfluidic system. A solid can be sprayed onto the substrate, or introduced as a suspension, after which the suspending liquid or gel can be evaporated or sublimated. The substrate can be placed in an atmosphere having analyte in a gaseous vapor.

The concentration of analyte introduced in solid, liquid, or gaseous form can be increased by various means before the analyte is introduced to the substrate, e.g., by filtering a solid, liquid, or gaseous mixture. The concentration can also be increased by coating the substrate with a second material which preferentially attracts the analyte under test.

Figure 14:
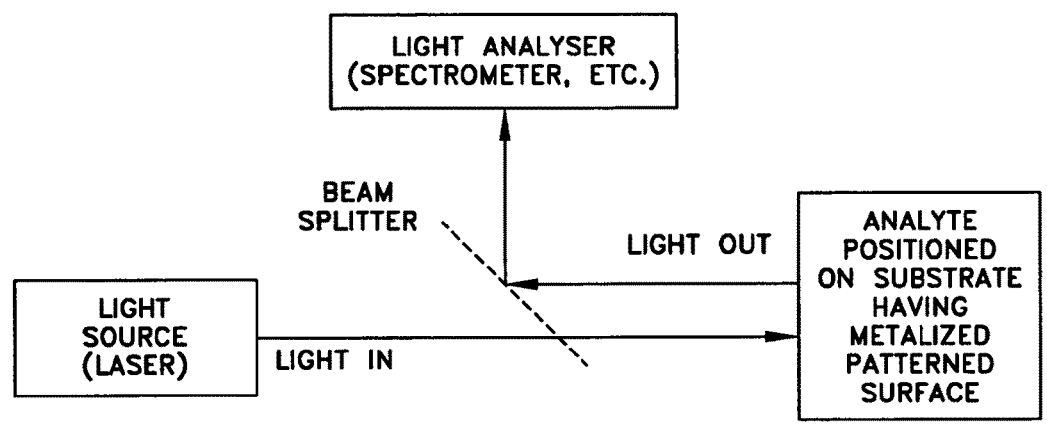
FIG. 14 is a schematic view showing a novel Raman spectroscopy system for performing a diagnostic assay on an analyte positioned on a substrate having a metalized patterned surface.

Once the analyte is introduced, the Raman spectrum can be recorded by irradiating the analyte with narrowband (e.g., laser) radiation. The incident radiation is usually focused on the sample and scattered radiation is usually collected with the same lens. An optical system with a dichroic beamsplitter can steer the scattered radiation out of the optical path taken by the incident radiation and to a spectroscope. See, for example, FIG. 14, which shows a Raman spectroscopy system for performing a diagnostic assay on an analyte positioned on a substrate having a metalized patterned surface. The resulting SERS spectrum that is collected can be analyzed in ways well known in the art to indicate what material is present and in what quantities. If the SERS cross-section is large enough, and the Raman spectrum has distinguishing features, this can be done with unlabeled molecules. If the amount of material is small, or its Raman spectrum is weak, the signal could be enhanced by binding another molecule that is labeled with an intensely photoactive dye prior to evaporation. If the sample could contain several molecules, several different labeled markers with distinct spectra could be used.

In order to work with the microarrays, the capability to dispense very small volumes of material is required. This technology is available, off-the-shelf, using piezoelectric dispensing equipment such as the Piezoarray from PerkinElmer, Inc. of Wellesley, Mass. for spotting picoliters (a 10 micron cube) or less.

A more involved detection starts with microarrays that are functionalized with various compounds such as unlabeled oligonucleotides or proteins or other ligands. These can be bound to the surface with a variety of techniques, including covalent bonds to the self-assembled monolayers previously described. Due to the specificity of the Raman spectrum, some assays can use non-specific functional conjugates, unlike for fluorescence assays. The analyte is introduced to the microarray and binding to the ligand is facilitated by one or more variables including time, temperature, or other factors. Unbound material is optionally washed away. Afterwards, a robotic Raman microscope then scans the array, much as current readers analyze genetic microarrays. The difference is that the recorded Raman spectrum would indicate not only the amount of bound material, but also what the material was. Since more than one material could be present in a given array location, a technique such as Principal Component Analysis (PCA) would be used to estimate which materials are present and their amounts. Depending on the amount of material and/or the Raman signal strength, either the functionalized substrate or the analyte could be labeled with one or more photoactive dyes.

Raman (and related IR) spectra cannot generally be used to identify the molecular structure of an unknown molecule, although some spectral features can be correlated to specific bonds or functional groups. However, the spectrum in total is a linear sum of all the Raman scattered light and can be analyzed for the presence and quantity of a particular compound. For simple molecular spectra and/or uncomplicated admixtures, measurements often use a single spectral peak characteristic of a compound that may be present, typically by fitting a peak at a given wavenumber with a simple profile that reflects the instrument response (typically Gaussian). For more complicated measured spectra, either due to complex molecular spectra or admixtures of different compounds, more complicated eigenmodes can be used to analyze the spectrum. In spectroscopy, Principal Component Analysis (PCA) is often used to quantify admixtures. In this approach, eigenvectors of the covariance matrix with large eigenvalues form a basis set used to deconvolve the measured spectrum using standard linear algebraic operations. With this technique, cross-correlations of the different molecular spectra, statistical frequency of the analytes, instrument response and noise characteristics can all be used to form an optimal estimate of the molecules present in a mixture and their concentrations.

Another potential application is in cell studies for signaling and expression of various proteins. In one application, the cells would eventually be plated and fixed onto a coarse array. Markers labeled with photosensitive dyes would then be washed with, and bound to, the target molecules. The cell membrane would be disintegrated and the cellular material would drop onto the substrate. A spatially-resolved Raman microscope could then detect the presence of the labeled markers with some correspondence to location in the cell.

Another possible application is use of the substrate for in-vivo cellular analysis. It is possible that suitably sharp nanospikes could serve as a bed of Raman-enhancing nails that could produce SERS signals from dye-labeled markers in live cells.

In order to perform dynamic assays, where the kinetics of binding are measured, the measurement device generally requires the capability to flow solutions over the nanostructured substrates. In some cases, library compounds will be flowed over substrates to which a target molecule is attached. This generally requires a microfluidic flow cell. The main requirement for this flow cell is that it must have an optically transparent window so the Raman sensing is not inhibited by the flow cell. Flow cells with channels that are laser machined in glass, as well as structures that use transparent polymers such as PolyDimethylSiloxane (PDMS) from which microfluidic structures can easily be fabricated. The signal levels must be matched to the measurement times so the integration times, which typically range from under 1 second to tens of seconds, can resolve the kinetics.

In order to achieve high throughput screening, several aspects of the instrumentation require optimization. This generally requires that the robotics move fast enough to keep any delays due to translation of the measurement apparatus relative to the array positions short compared to measurement times. Since the distances involved are quite small, this is generally not an issue for reasonable robotics (which can perform at the required accuracy with speeds of meters/second).

The most critical aspect is the multiplexing of detection capabilities. It is desirable to multiplex multiple spectral measurements on a single detector. The spectrometers used for Raman spectroscopy typically use a dispersive element, i.e., a grating. Typically, the grating is illuminated with a slit. If the illumination along the length of the slit comes from different sources that do not overlap, the spectrum will consist of multiple spectral strips from the different illumination sources.

Charge Coupled Devices (CCDs) for spectroscopy are available with millions of pixels and many are available with rectangular geometries. Depending on the number of multiplexed channels, a 1024×1024 or 1340×400 CCD, like those available from Princeton Instruments, Inc. of Trenton, N.J. may be a good choice. Multi-channel spectroscopy is well-known to the art—astronomers have been using multiplexed spectroscopes for many years, both ones that are fed with multiple discrete fibers and those that are imaging spectroscopes that can measure the spectrum of a linear image.

Another aspect of the multiplexing is the laser source. Lasers used for Raman spectroscopy generally require high spectral purity. Currently, lasers for Raman spectroscopy are available from multiple manufacturers with >350 mW of laser power. This should provide power for 10-100 multiplexed measurements in order to meet high-speed requirements.

There are engineering tradeoffs with systems that either image the microarray onto the sensor array or use discrete optical channels, e.g., multiple optical fibers. Among other things, there are tradeoffs of simplicity (separate fibers) versus packing density and optical throughput (reimaged microarray).

A performance goal of interest to the pharmaceutical industry is 100,000 measurements per instrument per day. This parameter is a familiar benchmark to pharmaceutical industry personnel doing lead discovery. For a nominal ten second measurement per array position, this benchmark would require 12 detection channels in parallel, assuming no time for the robotic motion. It can be achieved by using multiple fibers, and the corresponding instruments can take advantage of numerous optical components that have been developed for telecom applications that can handle multiple fiber inputs and outputs and do so with very regular positioning so no alignment is required.

There are other novel substrates being used for molecular analysis using Raman spectroscopy and SERS. Tienta Sciences, Inc. of Indiana offers Teflon coated substrates which concentrate solutions via surface tension and is working on adaptive silver films formed by controlled evaporated deposition for SERS. Mesophotonics Limited of Southampton, Hampshire, UK, is offering photonic crystal material for SERS. The approach described herein has significant advantages over the Tienta Sciences and Mesophotonics substrates, especially for microarrays. My approach is low cost while still retaining great flexibility to co-manufacture microarrays, microfluidic, and electrochemical features. My approach also has much greater control, through the laser pulse energy and polarization, than a controlled evaporation apparatus or a photolithography and etching process can economically achieve. The ability to do laser machining of the substrates adds a dimension that enhances the capabilities of my arrayed substrates. While photonic crystals offer good reproducibility and potential for microarrays similar to my approach, they are more expensive to manufacture. Moreover, the reproducibility relies on controlling a photolithography and etching process. Many manufacturers of MEMS devices have found that this can be costly to achieve in practice.

The approach described herein uses substrates with micro- and nanostructured surfaces created using femtosecond lasers. The femtosecond pulse deposits energy in the material faster than it can thermally diffuse. This gives rise to a variety of effects not possible with longer pulse laser processing. In the case of semiconductor and metal surfaces, it leads to formation of spikes. When the surface is processed in a gas, which may react with the substrate material, micron sized spikes with large aspect ratios (height/base) are formed. When the surface is processed in water or another liquid, nanometer-sized features are formed such as the remarkable surface structures shown in FIGS. 5-12.

Figure 5:
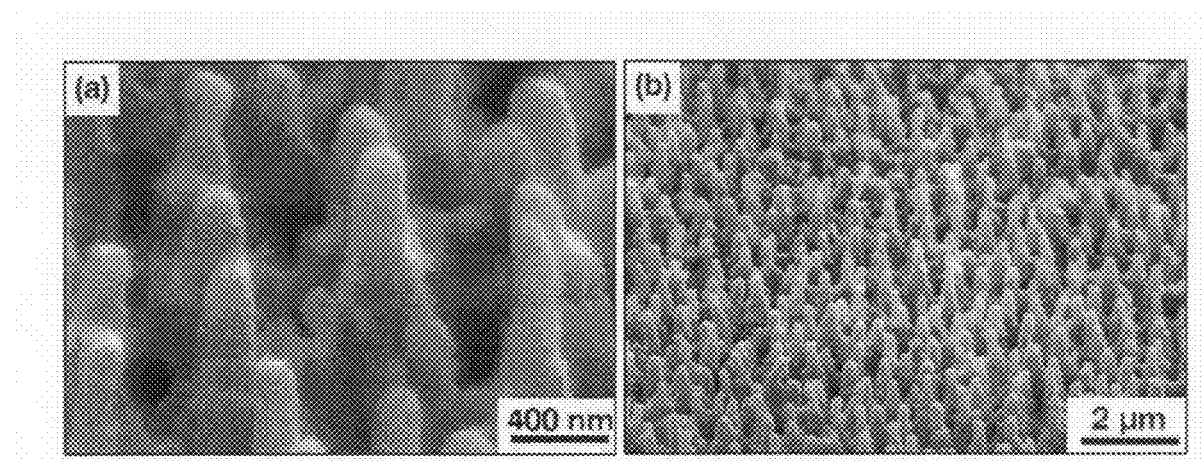
FIG. 5 is a schematic view of a nanostructured silicon surface formed by femtosecond laser irradiation at two different magnifications.
Figure 8:
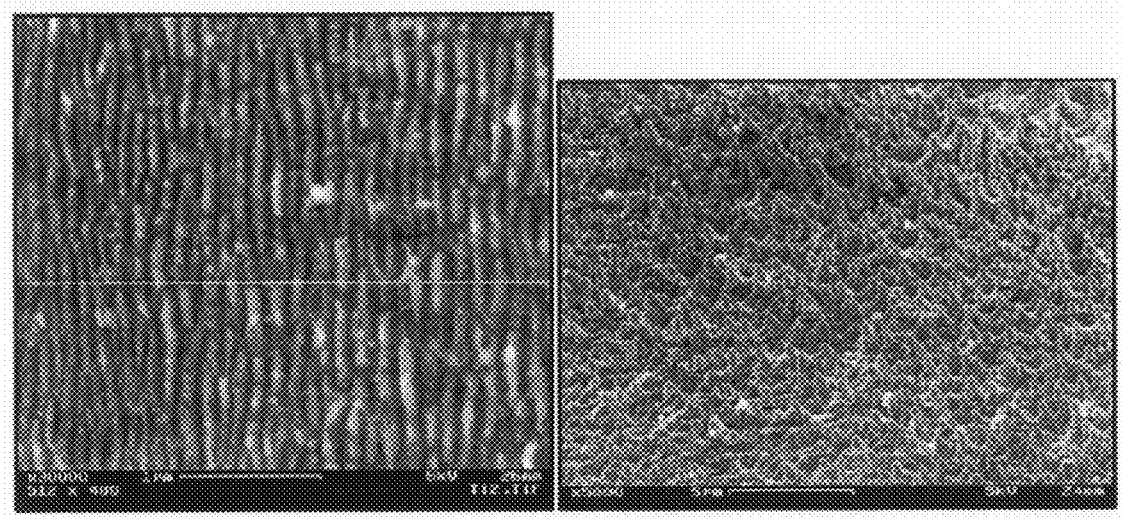
FIG. 8 is a schematic view of nanostructured metal surfaces formed by femtosecond laser irradiation—the left image shows a titanium surface and the right image shows a copper surface, and the scale bar is 1 µm at left, 5 µm at right.
Figure 9:
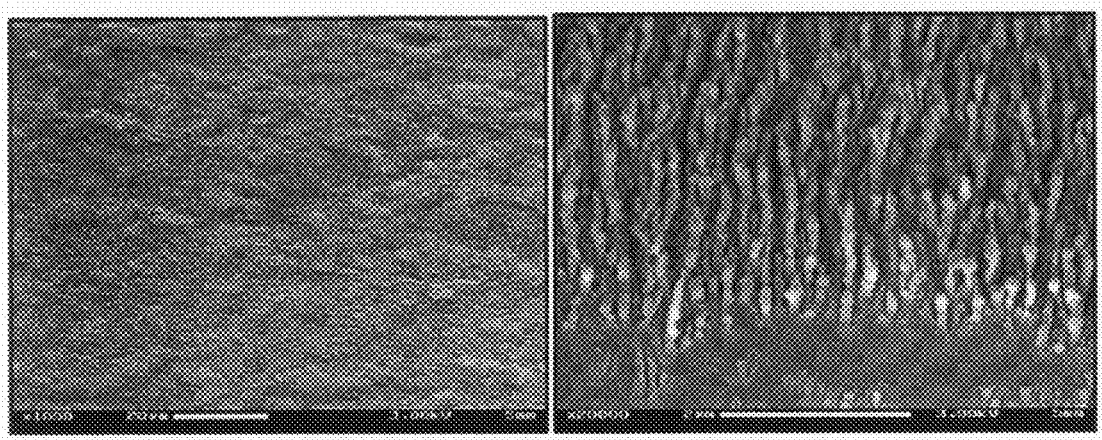
FIG. 9 is a schematic view of nanowires formed on silicon when the femtosecond laser processing is done with an organic solvent in place of water, which was used in the process shown in FIG. 5—the images of FIG. 9 show a surface processed with methanol, with the left image having a 20 µm scale bar, and the right image having a 2 µm scale bar, and being positioned at the edge of the region that was laser processed.
Figure 10:
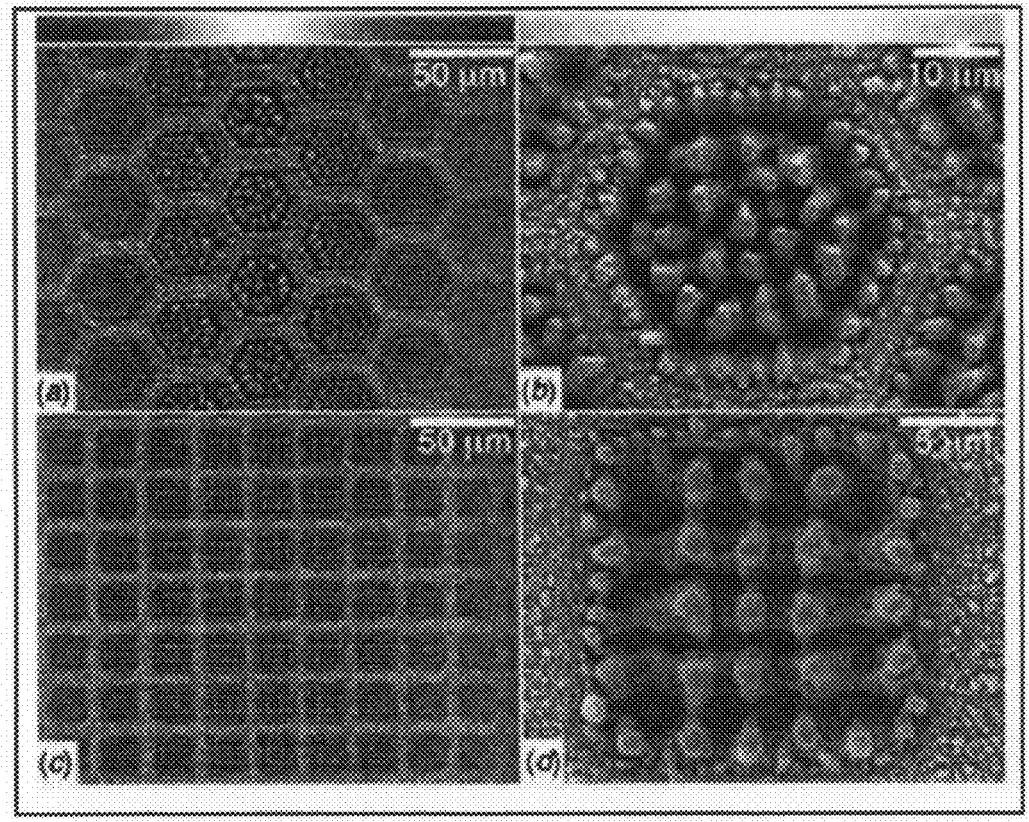
FIG. 10 is a schematic view of scanning electron micrographs of ordered silicon spikes formed by masking the irradiated sample with: (a) and (b), a 30 µm hexagonal grid, and (c) and (d), a 20 µm square grid, wherein the nearly Gaussian spatial intensity profile of the laser pulse is shown at the top in grayscale (white corresponds to maximum intensity)
Figure 11:
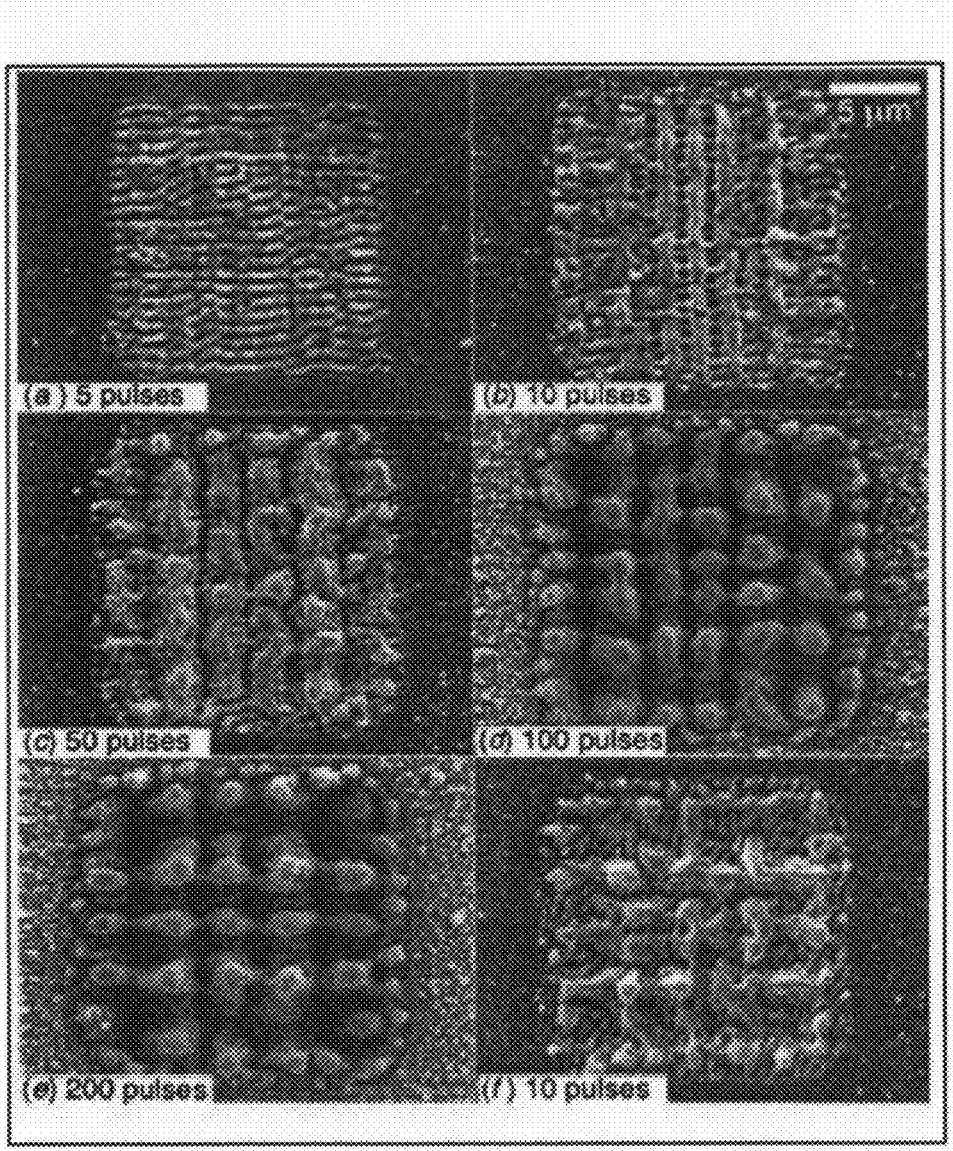
FIG. 11 is a schematic view of scanning electron micrographs of: (a)-(e), silicon spikes formed with a square grid after increasing number of laser pulses, wherein the direction of the electric field is vertical in (a)-(e), and with (f), spikes formed with the grid rotated 45° relative to the grids in (a)-(e)

FIG. 5 shows a silicon surface when the laser is normally incident to the surface. Here, the nanopatterned surface is an assembly of nanospikes. By changing the material, or the polarization and angle of the laser, a variety of different structures and scales can be formed. FIG. 8 shows the surface of two metals, titanium and copper, subject to the same laser processing. The titanium surface forms quasi-cylindrical ridges. The copper surface forms a less ordered assembly of nanospikes.

Figure 6:
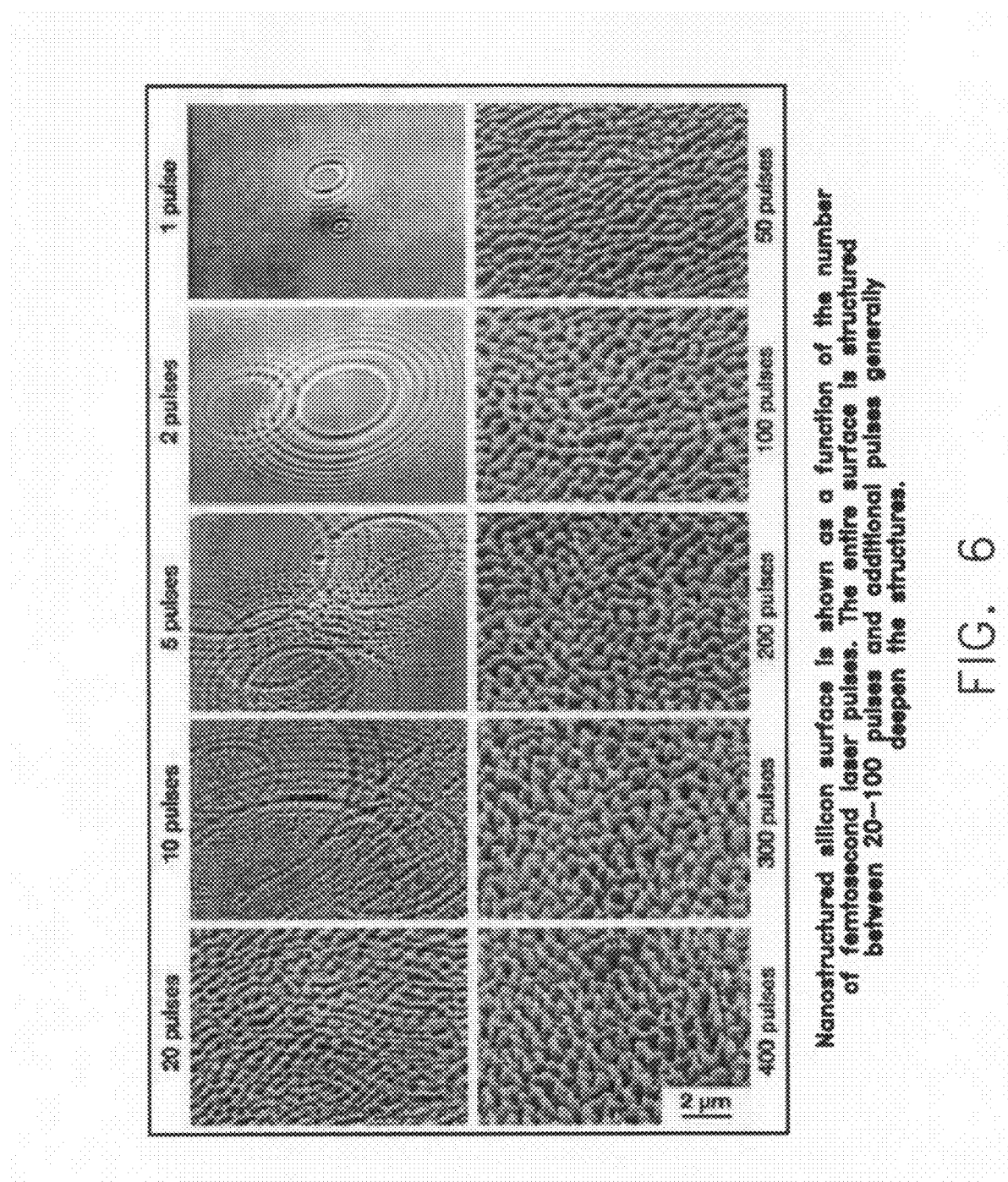
FIG. 6 is a schematic view of a nanostructured silicon surface, wherein the surface is shown as a function of the number of femtosecond laser pulses, wherein the entire surface is structured between 20-100 pulses and additional pulses generally deepen the structures.
Figure 7:
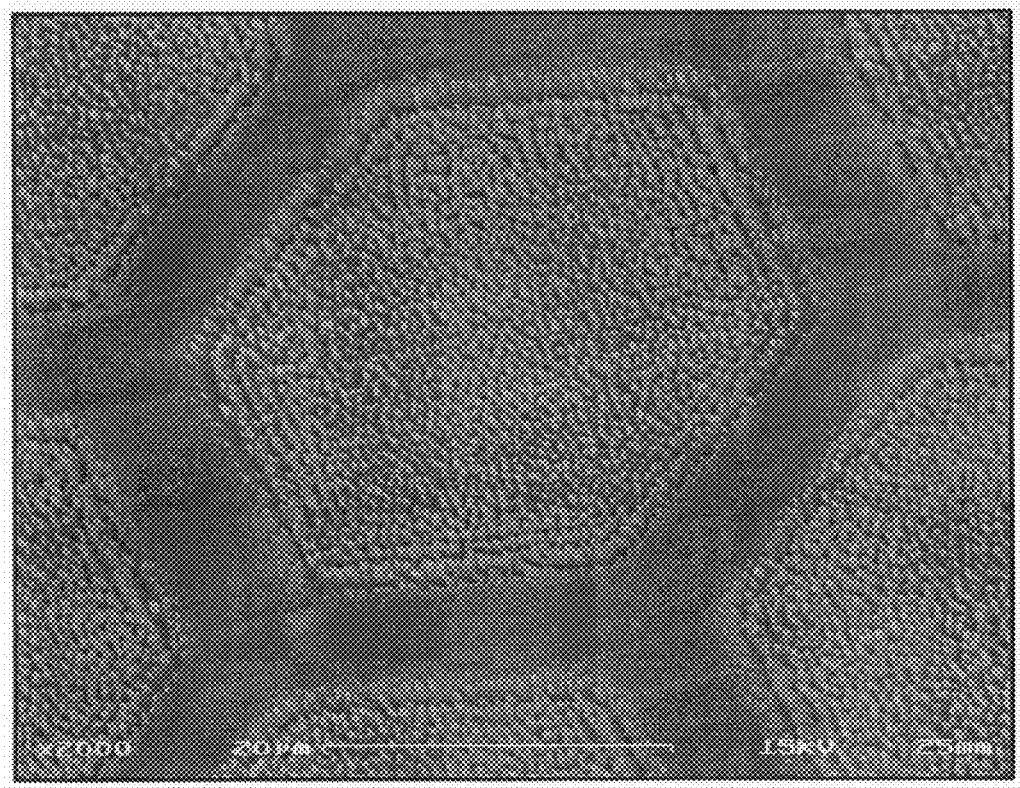
FIG. 7 is a schematic view of a stainless steel surface nanostructured with femtosecond laser pulses and micropatterned with a hexagonal mask—note that the structure near the mask boundary is partially ordered in rows while in the interior, the lateral structure of the surface is disordered.

The details of the laser nanopatterning process are not currently completely understood. However, it is generally thought that the laser excites a surface wave in the material, which propagates and is then frozen when the surface cools. Random variations in the melting of the surface layer, possibly due to asymmetry of the laser beam incident on the surface or irregularities in the surface material, has a stochastic effect after multiple laser pulses that produces the random surface with spiky features in silicon. This is seen in FIG. 6, where the progression of the surface, after increasing number of pulses, is shown.

There is a threshold which must be achieved in order for the nanoscale surface structuring to occur. Though it depends somewhat on the laser wavelength and base material, about $10 \text{ kJ/m}^2$ is required to excite the rippling process. In order to produce a surface with fully developed structure, a minimum number of pulses is required, on the order of 100. These two numbers combine to yield the surface area that can be processed per unit time as a function of average laser power, namely $1 \text{ mm}^2/\text{s}$ per Watt of average laser power.

This number is encouraging. While femtosecond lasers are not inexpensive, they certainly cost less than the equipment necessary to do semiconductor lithography on nanometer scales. The laser processing is much simpler than the various coating, exposure, and etching steps required when fabricating nanostructures lithographically. Consequently, these substrates will be less expensive to manufacture.

These materials can be micropatterned very easily. FIGS. 7-11 show micro- and nanostructured surfaces that have also been micropatterned. The patterning requires that a mask be placed on the surface of the material. The mask boundaries then naturally impress a pattern on the underlying micro- or nanostructure. Micropatterning can facilitate the efficient partition of the substrate into an array whereby the surface can be functionalized with an array of targets, similar to the microarrays used for fluorescence detection of oligonucleotide and other binding events. The surface structure can help confine analyte spotted onto the substrates.

The details of the structure inside the clear areas of the mask can show order as well. The structure can self-organize either due to the boundary condition imposed by the mask on the laser excitation, or due to the polarization of the laser, or a combination of the two. This property is of interest for SERS substrates since it is known that ordered structures can exhibit higher spectral selectivity or EM enhancement.

Figure 13:
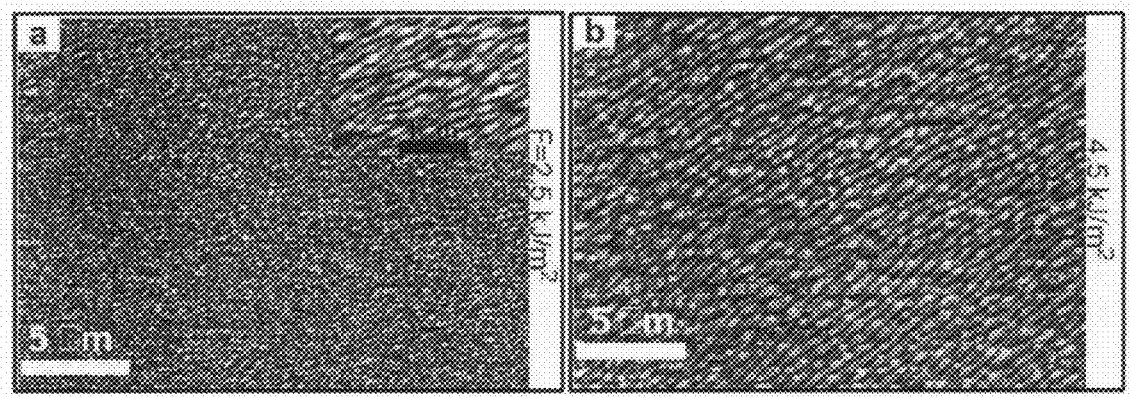
FIG. 13 is a schematic view of silicon nanostructured with femtosecond laser pulses, wherein the pulse energy increases from (a) to (b), as does the spatial scale of the structure, and the scale bar in the inset in (a) is 1 µm.

The statistical properties of the resulting surface are controlled by the parameters of the laser excitation. See, for example, FIG. 11, where the polarization vector, in combination with a mask, affects the order of the black silicon spikes. In FIG. 13, the lateral spatial scale of the structure is shown to be a function of the laser fluence per pulse. Larger fluence corresponds to larger structures. Similarly, the depth of the structures is a function of the fluence. Angling the surface relative to the laser also can help control both the fluence and the influence of the polarization vector on the symmetry of the surface (linear structures versus perpendicular spikes). These parameters enable us to tune the parameters of the surface, which in turn tunes the plasmon resonance that governs the coupling between the molecular vibrational modes and the laser light. In addition, the parameters of the surface structure can affect the conformational parameters of some molecules when they are adsorbed.

The nanostructured surfaces are produced by laser processing with femtosecond lasers. The details of these surfaces depend on a variety of factors. One is the environment surrounding the material when it is processed, namely the physical conditions. This can include temperature and pressure, in the case of a material processed in a gaseous environment. It can also include a transparent liquid that is covering the material when it is irradiated.

The laser processing itself offers many variables that affect the resulting nanostructure. First is the pulse energy. As the laser pulse energy is increased, the scale, both lateral and vertical, of the induced structure changes. For low energies, the ripples are smaller in both dimensions than for higher energies. It is well-known that the scale of the ripples affects the excitation of the surface plasmons by the laser, with spatial scales of ~200 nm giving good excitation with near IR wavelengths and smaller scales working better with shorter wavelengths. Thus, the pulse energy is a useful control to match the surface plasmon modes to the laser frequency.

Another variable is the material that is chosen. Possibly due to differing laser absorption and thermal properties, the aspect ratio of the nanostructures that are produced are very different for different materials. Silicon forms rather cylindrical features, while titanium forms smaller bumps and copper is somewhere in between.

It is possible to generate cylindrical structures where the cylinder axis is parallel to the surface, depending on the polarization of the input laser. These structures are predicted to have high enhancement at the boundary between cylinders where molecules may migrate, as the solvent dissolves.

All of these variables will affect how the resulting SERS enhancement varies with the morphology of the nanopatterned surface. The roughness of the nanopatterned surface will have some effect on how easy it is to functionalize for various reactions. The symmetry (i.e., whether there is a linear structure) will affect whether the polarization is significant and may affect molecular conformation.

Other features of the invention include the patterning of the substrate material. A micropattern can be created using a transmission mask, as were the patterned surfaces shown in the Figures. It is also possible to micropattern the surface by irradiating selected areas of the substrate with the laser. A laser spot focused to 25-50 microns can produce a structured region ~50 microns in diameter that is isolated from a neighboring structure 100-200 microns away. This density is of interest to biochip microarrays, especially when one considers that the selectivity of the Raman spectrum may allow some analysis to be performed with fewer array locations. These microarrays produced without a mask will have different operational and economic characteristics. They may cost less to manufacture, but the boundaries of the nanostructured regions may not be as sharp, and they will not exhibit the self-organized structures seen with transmission masks.

In addition to manufacturing the nanostructured surface directly by laser processing, a nanostructured surface may serve as a master from which nanostructured surfaces can be molded, or from which an intermediate negative master may be generated. A negative copy of the surface can be made by casting PDMS or another flexible material against the surface, which can reproduce nanostructured features of the surface with excellent fidelity. Although the resulting castings are more difficult to metalize than a semiconductor or metal, they are very inexpensive to fabricate.

In addition to the laser processing, other features of the substrates that will change their performance will depend on how the nanopatterned surfaces are metalized. The metalization material, whether silver, or gold, or another metal, will change both the SERS effect and the chemistry of the surface. The plasmon resonances are different for different metals. The chemistry may lead to different requirements when the surfaces are functionalized with oligonucleotides and ligands.

The properties of the metalization layer will also affect performance, depending on how the metalization is applied. One means of performing the metalization is by physical vapor deposition performed by evaporating the metalization material. The detailed structure of the metalization layer and the resulting SERS performance will vary depending on whether the evaporation is done by resistive heating, ion beams, sputtering, or other evaporation techniques. The metalization layer can also be applied by chemical or electrolytic deposition.

Another aspect to the metalization is control over the film geometry. Unlike many other metalized surfaces that have been used for SERS, some of the ones shown in the Figures are quite far from planar surfaces, either due to pillar-like structures or overall roughness. Consequently, the geometry of the evaporation will have a greater effect on the metal film that is deposited. One can induce a preferred axis by angling the substrate relative to the metalization source. Conversely, one may see different surface enhancement when the film on the sides of pillar-like structures is comparable to, or less than, the film on the tips.

The stability of the substrates over time will depend on how they are fabricated and stored. As the metalization layer may be reactive, sealed packaging is generally required to preserve the substrates over time.

The spectroscope used to detect Raman scattering also affects the sensitivity of the diagnostic. While commercial systems are available for as little as $10,000, without a microscope, more expensive systems will produce sharper spectra and will be more sensitive. Components and systems are available from multiple vendors such as InPhotonics, Inc. of Norwood, Mass. and Ocean Optics, Inc. of Dunedin, Fla., and lasers from vendors such as Coherent, Inc. of Santa Clara, Calif., and optical components are available from various component and filter vendors and will affect the system performance. The Raman spectrum can be measured using different illumination wavelengths and will interact with the surface characteristics vis-à-vis performance.

A variety of assays are possible with the apparatus that I have described. Similar assays have been performed with other SERS substrates. They include label-free detection of a biomolecule. One example relates to Anthrax. Another example is the label-free differentiation of human insulin and insulin lispro.

Another possible assay uses an array of genomic material. If a microarray is functionalized with various Raman labeled oligonucleotides, unknown genetic material can be introduced to react with the functionalized material and the unbound material washed away. The array, now with some spots including bound material and some spots without, is then scanned with the Raman spectrometer. The resulting data indicates where the unknown material bound with the spotted material and in what quantities.

Another possible assay involves proteomics. An example is to look for biotin-streptavidin binding. The substrate is functionalized with a ligand such as streptavidin. Unknown material, possibly containing biotin, which may be labeled with a dye such as Cy5, is reacted with the functionalized substrate and washed. Measurement of the resulting Raman spectrum indicates whether the unknown material contained the conjugate protein and in what quantities.

Another possible assay involves in-vivo cellular studies using SERS. This type of assay has been performed by injecting nano-sized metal particles into live cells. The injected particles serve as the plasmon resonators for SERS. One disadvantage of this process is that it is invasive to the cell. An in-vivo cellular assay using the substrate described herein relies on the spiky nature of the substrate to produce enhancement of the Raman signal even though the cell membrane lies between the substrate and the analyte within the cell. The enhancement factor will be reduced, due to the nanometer distance from the substrate to material within the cell, so this assay may not be as sensitive as one where the cell was killed and the membrane disintegrated.

Although various exemplary embodiments of the invention have been disclosed, it should be apparent to those skilled in the art that various changes and modifications can be made which will achieve some of the advantages of the invention without departing from the true scope of the invention. For example, other assays are possible that do not use SERS. There are several photonic effects that employ the interaction of electromagnetic fields, surface plasmons and molecules, of which SERS is only one example, that are possible with the substrates described herein. These effects and the corresponding assays and all such various embodiments, changes and modifications are to be understood to be within the scope of the present invention as described herein and as claimed in any appended claims.

What is claimed is:

1. Apparatus for use in performing a diagnostic assay of an analyte, the apparatus comprising:
    a base comprising at least one patterned surface, wherein the at least one patterned surface is characterized by structures ranging in scale from 10 to 2000 nanometers in all three spatial dimensions and further wherein the pattern is stochastic in all three spatial dimensions;
    the at least one patterned surface being created from a pre-patterned surface on the base by a laser process, wherein the resulting patterned surface has elevations both above and below the elevation of the pre-patterned surface; and
    a metal applied to the at least one patterned surface so as to provide at least one metalized patterned surface.

2. Apparatus according to claim 1 wherein the structures are selected from the group consisting of bumps, pillars, spikes, fissures and holes.

3. Apparatus according to claim 1 further comprising an optical characterization module comprising:
    a light source for directing light at an analyte disposed on the at least one metalized patterned surface; and
    a detector for measuring light scattered by the analyte.

4. Apparatus according to claim 1 wherein the base further comprises at least one unpatterned surface, with the structures of the patterned surface having elevations both above and below the elevation of the unpatterned surface.

5. An assembly comprising:
    a metal base comprising at least one patterned surface, wherein the at least one patterned surface is characterized by structures ranging in scale from 10 to 2000 nanometers in all three spatial dimensions and further wherein the pattern is stochastic in all three spatial dimensions;
    the at least one patterned surface being created from a pre-patterned surface on the base by a laser process, wherein the resulting patterned surface has elevations both above and below the elevation of the pre-patterned surface; and an analyte disposed on the at least one patterned surface.

6. An assembly according to claim 5 wherein the structures are selected from the group consisting of bumps, pillars, spikes, fissures and holes.

7. An assembly according to claim 5 further comprising an optical characterization module comprising:
 a light source for directing light at the analyte disposed on the at least one patterned surface; and
 a detector for measuring light scattered by the analyte.

8. A method for sensing at least one of the presence and quantity of an analyte, wherein the method comprises:
 providing a base comprising at least one patterned surface, wherein the at least one patterned surface is characterized by structures ranging in scale from 10 to 2000 nanometers in all three spatial dimensions and further wherein the pattern is stochastic in all three spatial dimensions, the at least one patterned surface being created from a pre-patterned surface on the base by a laser process, wherein the resulting patterned surface has elevations both above and below the elevation of the pre-patterned surface;
 applying a metal to the at least one patterned surface so as to provide at least one metalized patterned surface;
 positioning the analyte on the at least one metalized patterned surface; and
 performing a diagnostic assay of the analyte.

9. A method according to claim 8 wherein the nature of the patterned surface is regulated by beam control.

10. A method according to claim 8 wherein the nature of the patterned surface is regulated by structuring the laser light which is delivered to the base.

11. A method according to claim 10 wherein the laser light is split into two or more beams which are recombined at an angle so as to form a selected pattern on the base.

12. A method according to claim 10 wherein the laser light is passed through an optical mask before being delivered to the base.

13. A method according to claim 12 wherein the optical mask is deposited directly on the base.

14. A method according to claim 12 wherein the optical mask is spaced from the base.

15. A method according to claim 12 wherein fluid is passed through the gap which is located between the optical mask and the base.

16. A method according to claim 10 wherein a layer of inhomogeneous material is deposited on the base, and further wherein the inhomogeneous material has inhomogeneities on scales comparable to the resulting structures of the patterned surface.

17. A method according to claim 16 wherein the inhomogeneous material is a non-uniform light absorber.

18. A method according to claim 16 wherein the inhomogeneous material is a non-uniform light reflector.

19. A method according to claim 8 wherein the analyte comprises a fluid.

20. A method according to claim 8 wherein the analyte comprises a solid.

21. A method according to claim 8 wherein the base comprises a semiconductor.

22. A method according to claim 21 wherein the base comprises silicon.

23. A method according to claim 8 wherein the base comprises a metal.

24. A method according to claim 8 wherein laser processing is effected using a femtosecond laser.

25. A method according on claim 8 wherein laser processing is effected by delivering laser light to the base at a selected pulse rate, fluence, angle and/or polarization.

26. A method according to claim 8 wherein the at least one patterned surface comprises high-aspect ratio structures.

27. A method according to claim 8 wherein the at least one patterned surface is configured to provide large electric fields when the analyte is disposed on the at least one metalized patterned surface and energy is delivered to the analyte and/or the at least one metalized patterned surface.

28. A method according to claim 8 wherein the metal comprises a metal film.

29. A method according to claim 8 wherein the metal is selected from the group consisting of silver and gold.

30. A method according to claim 8 wherein the diagnostic assay comprises surface enhanced Raman spectroscopy, and further wherein the at least one metalized patterned surface provides the desired surface enhancement for the analyte.

31. A method for sensing at least one of the presence and quantity of an analyte, wherein the method comprises:
 providing a base comprising at least one patterned surface, wherein the at least one patterned surface is characterized by structures ranging in scale from 10 to 2000 nanometers in all three spatial dimensions and further wherein the pattern is stochastic in all three spatial dimensions, the at least one patterned surface being created from a pre-patterned surface on the base by a laser process, wherein the resulting patterned surface has elevations both above and below the elevation of the pre-patterned surface;
 positioning the analyte on the at least one patterned surface; and
 performing a diagnostic assay of the analyte.

32. A method according to claim 31 wherein the at least one patterned surface is subjected to a further processing step prior to use in performing a diagnostic assay, wherein the further processing step converts the at least one patterned surface into a substantially pristine layer.

33. Apparatus for use in performing a diagnostic assay of an analyte, the apparatus comprising:
 a base comprising a first surface and a second surface, the first surface being substantially planar and the second surface being characterized by structures ranging in scale from 10 to 2000 nanometers in all three spatial dimensions, the dimensions of the structures being substantially stochastic in all three spatial dimensions, the second surface being created from a portion of the first surface by a laser process such that the structures have elevations both above and below the plane of the first surface; and
 a metal applied to the at least one patterned surface so as to provide at least one metalized patterned surface.

34. Apparatus for use in performing a diagnostic assay of an analyte, the apparatus comprising:
 a base comprising an unpatterned surface and a patterned surface, the unpatterned surface being substantially planar and the patterned surface being characterized by structures ranging in scale from 10 to 2000 nanometers in all three spatial dimensions, with the pattern being stochastic in all three spatial dimensions, and with the structures having elevations both above and below the plane of the unpatterned surface; and
 a metal applied to the at least one patterned surface so as to provide at least one metalized patterned surface.

\* \* \* \* \*